(12) United States Patent
Matonick et al.

(10) Patent No.: US 10,792,042 B2
(45) Date of Patent: *Oct. 6, 2020

(54) CIRCULAR STAPLERS HAVING RESORBABLE MICRONEEDLES CONTAINING ACTIVE AGENTS

(71) Applicant: Ethicon, Inc., Somerville, NJ (US)

(72) Inventors: John P. Matonick, Warren, NJ (US); Robert J. Tannhauser, Bridgewater, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 1099 days.

This patent is subject to a terminal disclaimer.

(21) Appl. No.: 14/597,532

(22) Filed: Jan. 15, 2015

(65) Prior Publication Data
US 2016/0206865 A1 Jul. 21, 2016

(51) Int. Cl.
*A61B 17/00* (2006.01)
*A61B 17/115* (2006.01)
(Continued)

(52) U.S. Cl.
CPC .... *A61B 17/1155* (2013.01); *A61B 17/07292* (2013.01); *A61B 17/1114* (2013.01);
(Continued)

(58) Field of Classification Search
CPC .......... A61B 17/1155; A61B 17/07292; A61B 17/072; A61B 17/115; A61B 2017/1132; A61B 17/064; A61B 2017/07214; A61B 5/150984; A61B 17/068; A61B 17/1152; A61M 37/0015; A61M 2037/0061; A61M 2037/0023; A61M 2037/0046
See application file for complete search history.

(56) References Cited

U.S. PATENT DOCUMENTS

| 5,271,544 A | 12/1993 | Fox et al. |
| 5,411,508 A * | 5/1995 | Bessler ............... A61B 17/1114 227/179.1 |

(Continued)

FOREIGN PATENT DOCUMENTS

| EP | 1187653 | 3/2010 |
| WO | 2006049852 A2 | 5/2006 |
| WO | WO 2013/188884 | 12/2013 |

OTHER PUBLICATIONS

US 8,152,042 B2, 04/2012, Bettuchi et al. (withdrawn)
(Continued)

*Primary Examiner* — William R Carpenter
(74) *Attorney, Agent, or Firm* — David R. Crichton; Leo Kriksunov

(57) ABSTRACT

The present invention is directed to circular surgical staplers for anastomotic joining of tissue comprising a stapling head connected to an opposing anvil, said stapling head containing a plurality of deployable staples in concentric arrays; a plurality of resorbable medicant-releasing microneedles, the microneedles comprising elongated rods having a sharp tissue-penetrating distal end and a proximal end; with the microneedles releasably disposed on or within the stapling head or the anvil. The present invention is also directed to methods of use of such stapler devices.

7 Claims, 17 Drawing Sheets

(51) Int. Cl.
*A61K 9/00* (2006.01)
*A61B 17/072* (2006.01)
*A61B 17/11* (2006.01)
*A61M 37/00* (2006.01)
*A61B 90/00* (2016.01)
*A61B 17/064* (2006.01)

(52) U.S. Cl.
CPC ....... *A61K 9/0021* (2013.01); *A61M 37/0015* (2013.01); *A61B 17/072* (2013.01); *A61B 2017/00004* (2013.01); *A61B 2017/00893* (2013.01); *A61B 2017/0647* (2013.01); *A61B 2017/07257* (2013.01); *A61B 2017/07271* (2013.01); *A61B 2090/037* (2016.02); *A61M 2037/0046* (2013.01); *A61M 2037/0061* (2013.01); *A61M 2205/04* (2013.01)

(56) References Cited

U.S. PATENT DOCUMENTS

| | | | |
|---|---|---|---|
| 6,273,897 B1 | 8/2001 | Dalessandro et al. | |
| 6,325,810 B1 | 12/2001 | Hamilton et al. | |
| 6,334,856 B1* | 1/2002 | Allen | A61B 5/14514 128/898 |
| 7,744,624 B2 | 6/2010 | Bettuchi | |
| 7,972,357 B2 | 7/2011 | Bettuchi | |
| 8,016,849 B2 | 9/2011 | Wenchell | |
| 8,096,458 B2 | 1/2012 | Hessler | |
| 8,241,308 B2 | 8/2012 | Kortenback Ja et al. | |
| 8,281,975 B2 | 10/2012 | Criscuolo et al. | |
| 8,366,677 B2 | 2/2013 | Kaspar et al. | |
| 8,657,176 B2 | 2/2014 | Shelton, IV et al. | |
| 9,393,019 B2* | 7/2016 | Matonick | A61B 17/1155 |
| 2002/0082543 A1 | 6/2002 | Park et al. | A61N 1/30 604/21 |
| 2004/0044308 A1* | 3/2004 | Naimark | A61M 25/10 604/103 |
| 2005/0184121 A1* | 8/2005 | Heinrich | A61B 17/04 227/175.1 |
| 2006/0108393 A1* | 5/2006 | Heinrich | A61B 17/00491 227/179.1 |
| 2006/0271104 A1* | 11/2006 | Viola | A61B 17/00491 606/214 |
| 2007/0038181 A1 | 2/2007 | Melamud et al. | |
| 2007/0191811 A1* | 8/2007 | Berglund | A61M 25/104 604/509 |
| 2008/0082114 A1* | 4/2008 | McKenna | A61B 17/0643 606/153 |
| 2009/0001130 A1 | 1/2009 | Hess et al. | |
| 2009/0043250 A1 | 2/2009 | Gonnelli | |
| 2009/0062752 A1 | 3/2009 | Gonnelli | |
| 2011/0014181 A1 | 1/2011 | Thornton | |
| 2011/0147432 A1 | 6/2011 | Heinrich et al. | |
| 2012/0018487 A1* | 1/2012 | Bettuchi | A61B 17/072 227/175.1 |
| 2012/0241503 A1 | 9/2012 | Baxter, III et al. | |
| 2012/0241505 A1 | 9/2012 | Alexander, III et al. | |
| 2013/0008937 A1 | 1/2013 | Viola | |
| 2013/0068819 A1* | 3/2013 | Viola | A61B 17/068 227/176.1 |
| 2013/0331792 A1* | 12/2013 | Karp | A61M 37/0015 604/174 |
| 2013/0345671 A1 | 12/2013 | Ryu et al. | |
| 2014/0288386 A1* | 9/2014 | Zand | A61B 5/14552 600/301 |
| 2016/0206864 A1* | 7/2016 | Matonick | A61B 17/072 |

OTHER PUBLICATIONS

Jonsson, Kent, et al. "Breaking Strength of Small Intestinal Anastomoses", The American Journal of Surgery, vol. 145, Jun. 1983, pp. 800-803.

Yun Yang, Seung et al. "A Bio-Inspired Swellable Microneedle Adhesive for Mechanical Interlocking with Tissue", Nat Commun. vol. 4, 1702, Apr. 16, 2013, pp. 1-21.

Hong, Xiaoyun, et al, "Dissolving and Biodegradable Microneedle Technologies for Transdermal Sustained Delivery of Drug and Vaccine", Drug Design, Development and Therapy, vol. 2013, issue 7, pp. 945-952.

Yeu-Chun, Kim, et al. "Microneedles for Drug and Vaccine Delivery", Advanced Drug Delivery Reviews, vol. 64, 2012, pp. 1547-1568.

Yik-Hong, Ho, et al. "Techniques for Colorectal Anastomosis", World Journal Gastroenterol, Apr. 7, 2010, vol. 16, issue 13, pp. 1610-1621.

International Search Report dated Apr. 11, 2016 for Application No. PCT/US2016/013134.

\* cited by examiner

CIRCULAR STAPLERS HAVING RESORBABLE MICRONEEDLES CONTAINING ACTIVE AGENTS

FIELD OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Patent Application No. 2013/0068819 entitled "Structure Containing Wound Treatment Material", discloses an anvil assembly for a circular stapling apparatus, where the anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The wound treatment material is at least one of an adhesive, a sealant, a hemostat and a medicament.

U.S. Patent Applications Nos. 2011/0147432 and 2006/0108393, both entitled "Structure for applying sprayable wound treatment material", relate to surgical instruments, structures and methods for enhancing the properties of tissue to be repaired or joined and disclose a surgical stapling apparatus including a wound treatment material dispersion system for delivering wound treatment material to a target surgical site. The dispersion system includes an aperture formed in the anvil assembly oriented to dispense wound treatment material in an outward direction; and a source of wound treatment material in fluid communication with the aperture of the anvil assembly.

U.S. Patent Application No. 2011/0014181 entitled "Microneedle Delivery Device and Methods of Using Same" describes microneedle bioactive agent delivery systems, associated apparatus and methods of using such. The microneedles described are deliverable using a needle or syringe apparatus that can interface with existing medical devices or the devices can be used as standalone systems. The systems deliver at least one bioactive agent to a tissue in need thereof, for example, the myocardium.

U.S. Patent Application No. 2007/0038181 entitled "Method, system and device for delivering a substance to tissue" discloses devices and methods for delivering a substance to tissue or organs, particularly, the bladder, by a plurality of microneedles. The devices may include a delivery tube, a substance chamber to fill with the substance to be delivered, a plurality of needles, a plunger coupled to a handle movable relative to the tube to deliver the substance to the tissue through the needles, and a protective plate having at least one orifice therein, such that when the device is in a first, resting, position the needle tips are on a first side of the protective plate, and when the device is in a second, operational, position, the needles are on a second side of the protective plate.

U.S. Pat. No. 8,281,975, entitled "Surgical apparatus and structure for applying sprayable wound treatment material" discloses an apparatus for forming an anastomosis between adjacent sections of tissue. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

U.S. Pat. No. 8,152,042 entitled "Annular Adhesive Structure" discloses an apparatus for sealing at the anastomotic site. In some embodiments, a washer or structural body is wrapped completely around an anvil shaft, with staples driven through the structural body to release the sealant.

U.S. Pat. No. 7,972,357 entitled "Extraluminal sealant applicator and method" and U.S. Pat. No. 7,744,624 disclose apparatus for applying sealant to a target tissue of a surgical site. The apparatus includes a handle, a conduit and an end effector. The handle has means configured and adapted for operating the end effector and dispensing biological sealant to the surgical site via the end effector. The conduit stores and/or carries sealant towards the end effector. The end effector is configured to clamp around a body organ or tissue and apply and confine biological sealant in a substantially uniform manner. More specifically, the references disclose a system for applying sealant to a target tissue of a surgical site, comprising: a two-part sealant comprising a first part and a second part; an apparatus comprising: a handle; an end effector in operative association with the handle, the end effector including a first jaw member, a second jaw member, and a sealant-applying structure configured for applying sealant to the target tissue; the first jaw member being in fluid communication with a first conduit and a second conduit to convey sealant to the sealant-applying structure; the second jaw member being in fluid communication with a third conduit and a fourth conduit to convey sealant to the sealant-applying structure; the first and third conduits configured for conveying the first part of the two-part sealant to the sealant-applying structure; and the second and fourth conduits configured for conveying the second part of the two-part sealant to the sealant-applying structure.

U.S. Pat. No. 8,096,458 entitled "Pouch used to deliver medication when ruptured" describes a surgical stapling device, comprising: a handle portion; an elongate body portion; and a head portion located at the distal end of the body portion, the head portion including an anvil assembly, a staple cartridge assembly and a knife blade, the staple cartridge assembly having an annular array or group of staples, the anvil assembly being connected to the body portion along a shaft, the anvil assembly including: an anvil plate defining a plurality of staple forming pockets therein and a recess; and a wound treatment material disposed substantially within the recess.

U.S. Pat. No. 8,241,308 entitled "Tissue fastening devices and processes that promote tissue adhesion" discloses a fastener for fastening tissue segments having tissue surfaces, the fastener comprising: a first fastener member defining a fluid opening configured to receive a therapeutic agent, a plurality of fluid ports configured to deliver the therapeutic agent to the tissue segments, and a passageway between the fluid opening and the plurality of fluid ports; and a second fastener member having a substantially flat base and a post extending from the base proximate a center of the base, the post defining an opening for receiving and retaining the first fastener member such that the tissue segments to be fastened are retained between the first and second fastening members, the substantially flat base extending radially beyond a periphery of the post; wherein a longitudinal axis extends through the fluid opening, the fluid ports being radially arranged about the axis.

U.S. Pat. No. 8,366,677 "Microneedle arrays formed from polymer films" discloses a transdermal delivery device, comprising: a polymer base layer having microneedles projecting from a surface thereof, wherein the microneedles are compositionally homogenous with the polymer base layer, and wherein the microneedles of the transdermal delivery device are configured to be left in a skin surface of a subject to provide sustained delivery of an active agent even after removal of the polymer base layer, and wherein the polymer of the polymer base layer and the microneedles is polyvinyl alcohol.

U.S. Pat. No. 8,016,849 discloses a surgical apparatus, comprising: a first half-section having a distal end and a proximal end, the first half-section being adapted to receive a disposable loading unit in the distal end thereof; a second half-section in juxtaposed relation to the first half-section, the second half-section having a distal end and a proximal end; a disposable loading unit selectively operatively engageable with the distal end of the first half-section, the disposable loading unit including: a cartridge; a plurality of deployable needles supported within the cartridge, wherein each needle includes a lumen extending there through, and at least one hole formed in an outer periphery thereof for radially dispensing a fluid; a needle pusher in operative association with each needle for sequentially deploying each needle from the cartridge and into a target tissue; and an actuation member translatably disposed within the cartridge for delivering a driving force to each needle pusher to deploy the needles from the cartridge; and a wound treatment material applicator assembly for delivering a wound treatment material to the target surgical site, the applicator assembly including: a respective reservoir supported on an outer periphery of the distal end of each of the first and second half-sections, wherein the wound treatment material is disposed within each reservoir and at least one of the reservoirs is in direct fluid communication with the plurality of deployable needles.

U.S. Patent Publication No. 2005/0184121 discloses a surgical stapler comprising: a first jaw adapted to receive a staple cartridge in a distal end of the first jaw, the staple cartridge containing a plurality of individual surgical staples, and having a working surface with a plurality of staple slots formed therein; a second jaw having a staple anvil in a distal end of the second jaw, such that during the operation of the surgical stapler the staple cartridge and the staple anvil can be approximated relative to one another; a driving member for firing the surgical staples from their staple slots and against the approximated staple anvil; a body tissue property enhancing system for enhancing one or more properties of body tissue to be repaired or joined by the surgical stapler, the body tissue property enhancing system including: a biocompatible wound closure material dispensing system for dispensing an amount of surgically biocompatible wound closure material to a target staple site during at least one of prior to, after and concomitant with a firing of the surgical stapler to expel the plurality of staples loaded in the staple cartridge, the body tissue property enhancing system comprising at least one reservoir disposed in the staple cartridge for containing the biocompatible wound closure material therein; a plurality of ducts formed in the staple cartridge, wherein the plurality of ducts communicate with and extend from the at least one adhesive reservoir to the working surface of the staple cartridge; and a plurality of deployable needles each having a tip, the needles being adapted and disposed in the ducts of the staple cartridge such that their tips can be extended out of the working surface of the staple cartridge to penetrate at least a layer of the adjacent layers of body tissue and to allow the biocompatible wound closure material to be delivered along the exterior of the needles to penetrate one or more layers of the body tissue.

U.S. Patent Publication No. 2013/0008937 discloses a surgical stapling apparatus for joining body tissue, comprising: a staple anvil positioned at a distal end of the stapling apparatus and having a knife track defined therein; a staple cartridge positioned adjacent the staple anvil, the staple cartridge and staple anvil being juxtaposable relative to each other, the staple cartridge including a plurality of surgical staples individually disposed within individual staple slots formed in rows in the staple cartridge, and having a knife slot formed between adjacent rows of staples; a driving member for firing the surgical staples from the individual staple slots and against the staple anvil; a staple actuator having at least one cam wedge for ejecting staples and a knife blade, the staple actuator being movable along the staple rows; and a wound closure material applicator assembly operatively associated with the stapling apparatus, the assembly including: a conduit for conveying a wound closure material from a location external of the staple anvil and the staple cartridge to the staple actuator, wherein the conduit extends proximally from the staple actuator; and a distribution tip in communication with the conduit and having an orifice, the conduit and the distribution tip being attached to the staple actuator so that the conduit and the distribution tip move along the staple rows with the staple actuator.

Published PCT Patent Application No. WO2013/188884 discloses a wound closure device comprising one or more microstructure arrays, each comprising at least two microstructures. In some aspects, at least one microstructure is capable of penetrating into tissue and holding it in place. In some aspects, the microstructures are microneedles.

Published European Patent Application No. EP 1,187,653 discloses a device for transport of a material across or into a biological barrier comprising a) a plurality of hollow microneedles each having a base end and a tip, with at least one hollow pathway disposed at or between the base end and the tip, b) a substrate to which the base ends of the microneedles are attached or integrated, and c) at least one reservoir which is in connection with the base ends of at least one of the microneedles, either integrally or separably until the moment of use, wherein the volume or amount of material to be transported can selectively be altered.

U.S. Patent Publication No. 2009/0043250 discloses membrane containing microneedles, microneedle arrays, and needles.

U.S. Patent Publication No. 2009/0062752 discloses a microneedle device, comprising a first layer formed into the shape of a microneedle and comprising a material suitable for piercing tissue, and a second layer having a switch formed thereon and capable of being coupled into electrical communication with microneedle.

U.S. Patent Publication No. 2013/0345671 discloses a drug delivery device for attachment to the outer wall of a blood vessel, the blood delivery device comprising: a) a body made of a biocompatible material and formed so as to cover the blood vessel; b) one or more needles made of a biocompatible material, which are connected to the inside of the body and inserted into the tunica media of the blood vessel so as to deliver a drug to vascular smooth muscle cells; c) one or more drug reservoirs formed in the body; and d) microchannels formed in the needles and serving to deliver the drug from the drug reservoirs to the tunica media of the blood vessel.

An article titled "Dissolving and biodegradable microneedle technologies for transdermal sustained delivery of drug and vaccine" by Xiaoyun Hong et al., Drug Design, Development and Therapy 2013:7, pp. 945-95, provides an overview of microneedle technology, disclosing that dissolving and biodegradable microneedle technologies have been used for transdermal sustained deliveries of different drugs and vaccines. The review describes microneedle geometry and the representative dissolving and biodegradable microneedle delivery methods via the skin, followed by the fabricating methods.

An article titled "A Bio-Inspired Swellable Microneedle Adhesive for Mechanical Interlocking with Tissue", by Seung Yun Yang et al., Nat Commun. 2013, 4, p. 1702 discloses a biphasic microneedle array that mechanically interlocks with tissue through swellable microneedle tips, achieving increase in adhesion strength compared to staples in skin graft fixation, and removal force of about 4.5 N/cm2 from intestinal mucosal tissue and comprising a poly(styrene)-block-poly(acrylic acid) swellable tip and non-swellable polystyrene core, conical microneedles penetrate tissue with minimal insertion force and depth, yet high adhesion strength in their swollen state.

An article titled "Microneedles for drug and vaccine delivery" by Yeu-Chun Kim et al., Adv Drug Deliv Rev. 2012, 64(14), pp. 1547-1568, provides an overview of microneedle technology, disclosing that microfabrication technology enabled microneedle manufacture as (i) solid microneedles for skin pretreatment to increase skin permeability, (ii) microneedles coated with drug that dissolves off in the skin, (iii) polymer microneedles that encapsulate drug and fully dissolve in the skin and (iv) hollow microneedles for drug infusion into the skin. Microneedles have been used to deliver a broad range of different low molecular weight drugs, biotherapeutics and vaccines, including published human studies with a number of small-molecule and protein drugs and vaccines. Influenza vaccination using a hollow microneedle is in widespread clinical use and a number of solid microneedle products are sold for cosmetic purposes. In addition to applications in the skin, microneedles have also been adapted for delivery of bioactives into the eye and into cells.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult. Other technologies attempt to deliver the materials upon deploying of the stapler, resulting in complex equipment which delivers materials into highly compressed tissue. There is a need in improving delivery of therapeutic agents to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site, especially when sealing an anastomosis between adjacent intestinal sections so as to improve tissue viability and to prevent leakage.

The present invention, in one aspect, relates to a circular surgical stapler for anastomotic joining of tissue having a stapling head connected to an opposing anvil, with stapling head containing a plurality of deployable staples in concentric arrays. A plurality of resorbable medicant-releasing microneedles, comprising elongated rods having a sharp tissue-penetrating distal end and a proximal end, are releasably disposed on or within the stapling head or the anvil.

The microneedles are configured to be left in the tissue layers after joining of the tissue layers. In some aspects, the microneedles are disposed on a tissue-facing surface of the stapling head on a periphery of the stapling head and outside of the concentric arrays of the deployable staples. The microneedles can further comprise a barb at the distal end thereof and installed substantially perpendicularly to the tissue-facing surface. In certain aspects, the microneedles are releasably supported by an attachment strip disposed on the tissue-facing surface. The attachment strip can be a compressible foam layer, with microneedles embedded within the compressible foam layer.

In some aspects, the microneedles are supported by a buttress or a tissue thickness compensator releasably disposed on the tissue-facing surface.

The medicant can be a drug, an enzyme, a growth factor, an anti-inflammatory agent, a vasodilating agent, a peptide, a protein, a nutrient, an excipient, a cell, or combinations thereof. The medicant can be released over a period of from about 2 hours to about 4 weeks, more preferably from about 4 hours to about 5 days, most preferably from about 4 hours to about 3 days. The stapling head has at least 10 microneedles with microneedles being from 50 microns to about 1000 microns in diameter and from about 100 microns to about 2500 microns long. The present invention also relates to a method of joining tissue using a circular surgical stapler, having the steps of axially positioning the stapling head within a first tubular tissue and the anvil within a second tubular tissue and connecting the stapling head with the anvil; approximating the stapling head with the anvil thus compressing the first and the second tissue between the stapling head and the anvil; deploying the microneedles into the first and the second tissue; simultaneously or consecutively deploying the plurality of staples into the tissue layers thus closing or joining the first and the second tissue; opening the stapler and removing the stapling head and the anvil from contact with the first and the second tissue, allowing the microneedles to stay in the first and the second tissue such that the medicant is released over time into the tissue layers in the vicinity and/or adjacent to the microneedles.

DETAILED DESCRIPTION OF THE INVENTION

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-op leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Figure 1:
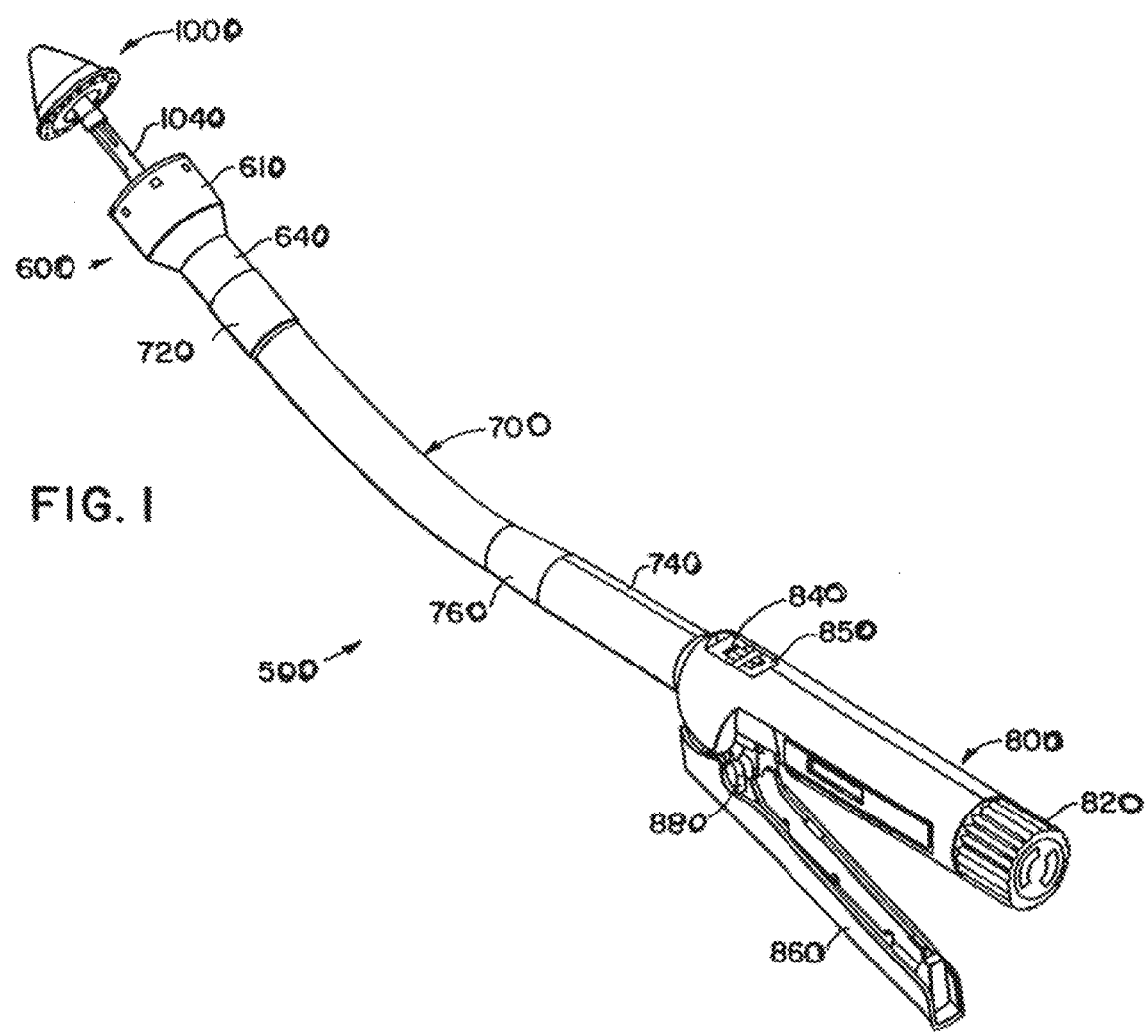
FIG. 1 shows prospective view of a typical circular surgical stapling instrument

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. An optional movable indicator 840 is visible through an optional window 850 on top of the handle assembly 800 to indicate the staple height selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

According to the present invention, application of therapeutic material or medically useful agents or medicants to tissue layers is performed via insertion into the tissue, including insertion into subserosal tissue, of soluble or resorbable microneedles containing the medicants. The insertion of the microneedles containing the medicants into the tissue is performed immediately before the joining of the tissue by staples (i.e. before deploying of the staples into the tissue), or simultaneously and synchronously with the joining of the tissue by staples, and is performed by using the same surgical stapler that deploys the staples. The medicants are then released from soluble or resorbable microneedles into the surrounding tissue over time, such time ranging from a few hours to several days to several weeks, such as 12 hours, 24 hours, 48 hours, 1 week, 2 weeks, 4 weeks, with such medicant release referred to as sustained release of medicants. Time of medicant release is generally not longer than about 4 weeks. The soluble or resorbable microneedles will fully dissolve or fully resorb over a period of microneedle resorption, which can be same as the time of medicant release, or longer than the time of medicant release, such as 24 hours, 48 hours, 1 week, 2 weeks, 4 weeks, 6 weeks, but in general not longer than about 6-8 weeks.

Therapeutic material or therapeutic agent or medicant refers to any medically useful substance or combination of substances, which can improve tissue viability, including drugs, enzymes, growth factors, peptides, proteins, nutrients, excipients, antimicrobial agents, and any other injectable pharmaceutical agents. Of particular interest are medicants such as growth factors, vasodilators, and antithrombotic agents. Other examples of therapeutic agents are also autologous cells and fibrinogen.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jonsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

According to the present invention, the tissue is treated with medicants outside of the staple line, not within the staple line, in order to improve the outcomes for the stapled tissue recovery. The present invention discloses embodiments of surgical staplers delivering soluble or resorbable microneedles outside of the staple line, with the microneedles impregnated and/or coated with the medicants, with the microneedles delivered immediately before or simultaneously with the stapling and left in the tissue to release the active agents or medicants. The microneedles are injected/inserted into tissue by the action of the stapler, preferably the microneedles are inserted into both layers of tissue being stapled together. The microneedles are left in the tissue for immediate and/or delayed or sustained release of medicants, and the microneedles eventually fully dissolve or resorb within the tissue.

According to the present invention, the stapling head or anvil of the circular anastomosis stapler has a plurality of solid, optionally barbed implantable and resorbable microneedles which are inserted into the tissue by the action of the stapler.

Figure 2:
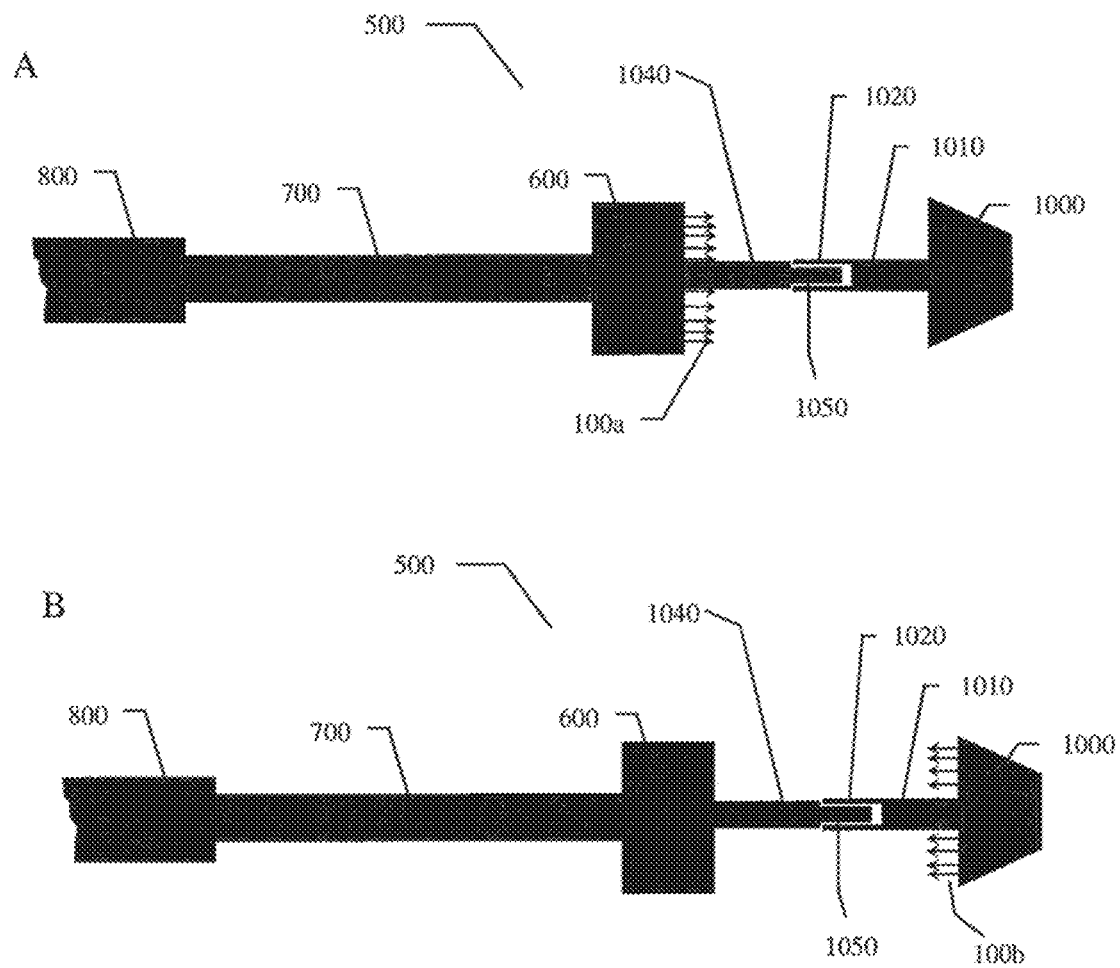
FIG. 2 shows schematic side view of one aspect of the circular stapler of the present invention.

Referring now to FIG. 2, a schematic side view of circular anastomotic stapler 500 is shown, with stapling head assembly 600 and anvil assembly 1000 connected by a support shaft assembly 700 to a proximal actuator handle assembly 800. The anvil assembly or anvil 1000 is slidable longitudinally relative to the stapling head assembly 600 and is mounted on an axially extending moveable shaft 1040. Typically anvil 1000 is connected in a lockable way to axially extending moveable shaft 1040 extending from stapling head 600. Anvil 100 connection to shaft 1040 is typically established via anvil pin 1010, locking for instance through engagement of a shaft 1040 tip 1050 into a sleeve 1020 formed in anvil pin 1010. Other ways of engaging and locking anvil 1000 to shaft 1040 are known. Staples and aspects of staple delivery are not shown for simplicity.

As shown in FIG. 2A, in one aspect, microneedles 100a are disposed on stapling head assembly 600 facing towards anvil assembly 1000. As shown in FIG. 2B, in another aspect, microneedles 100b are disposed on the anvil assembly 1000 facing towards stapling head assembly 600. In the further description of preferred embodiments, microneedles are shown only disposed on stapling head assembly 600.

Figure 3:
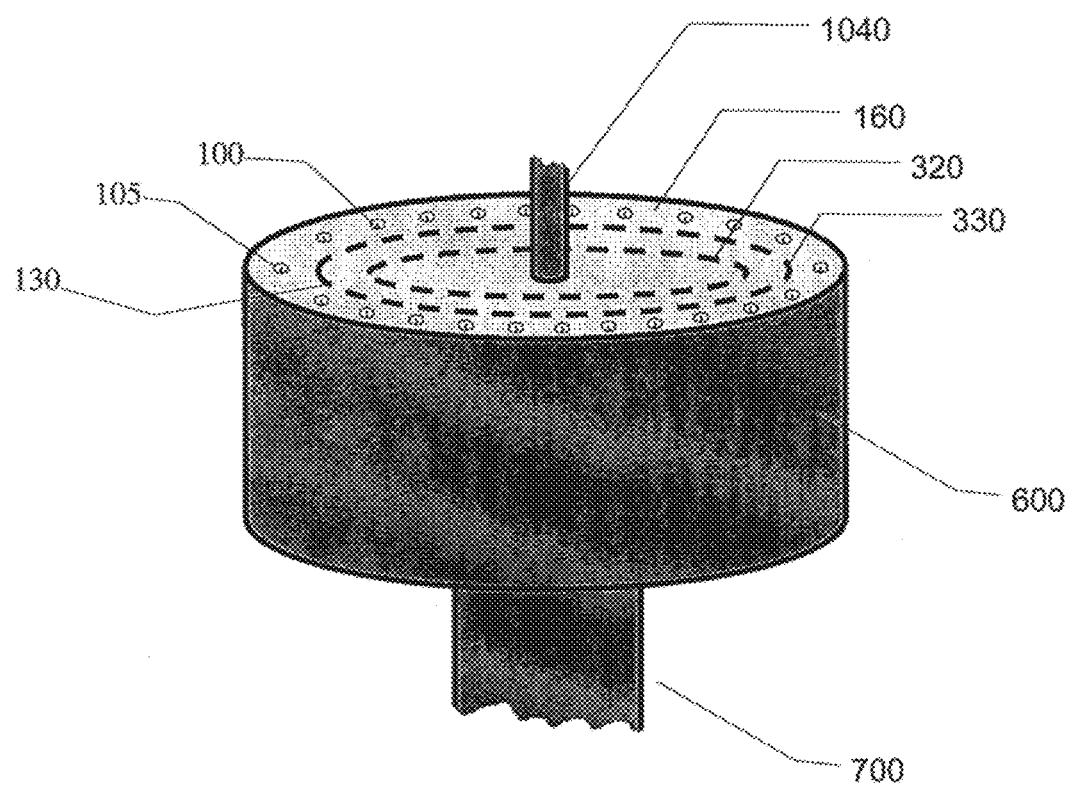
FIG. 3 shows schematic prospective view of one aspect of the circular stapler of the present invention.
Figure 4:
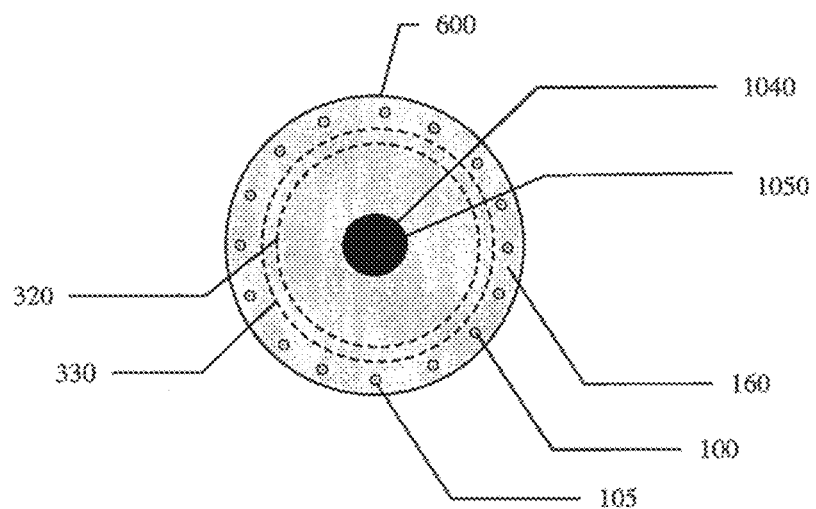
FIG. 4 shows schematic top view of one aspect of the circular stapler of the present invention.
Figure 5:
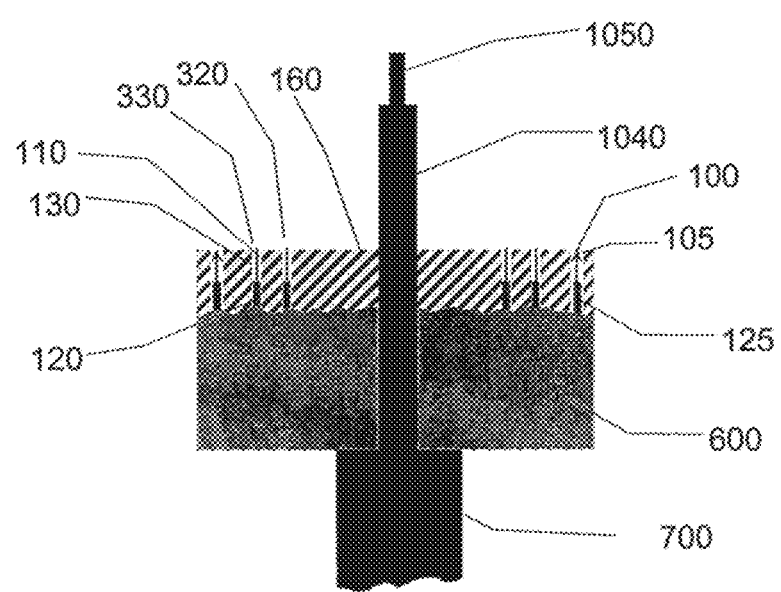
FIG. 5 shows schematic side cross-sectional view of one aspect of the circular stapler of the present invention.

Referring now to FIGS. 3, 4, and 5, which are showing respectively, a schematic prospective view, a schematic top view, and a schematic cross-sectional side view of one aspect of stapling head assembly 600 of the present invention. Stapling head 600, in one aspect, has a plurality of solid, optionally barbed implantable microneedles 100 which are inserted into the tissue by the action of the stapler. Microneedles are deployed in wells 105 similar to the staples wells and pushed into the tissue by the same mechanism as the staples. This embodiment requires modification of the commonly used stapling head assembly 600 to add an array of microneedle filled wells 105. Microneedles 100 are deployed similarly to staples and simultaneously with the staples by the same mechanism. Preferably microneedles are in a form of elongated pins with sharp barbed tips. Alternatively, microneedles can be in a form of a "U"-shape, similar to the staple, but with legs shorter vs. the metal staples.

Stapling head 600 has tissue facing surface 160, which is facing towards anvil assembly. On tissue facing surface 160 are positioned concentric stapling lines 320 and 330 surrounding moveable shaft 1040. Concentric array of microneedles 100 is positioned on tissue facing surface 160 around the larger stapling line 330 on the periphery of stapling head assembly 600, and distally from moveable shaft 1040.

Channels 130 contain staples 110 and staple advancers 120, with the staples 110 configured to advance through channels 130 into the tissue when pushed by staple advancers 120. A plurality of soluble or resorbable microneedles 100 containing the medicants, designated as microneedles 100, are positioned within wells 105 arranged concentrically around the larger stapling line 330 on the periphery of stapling head assembly 600, and distally from moveable shaft 1040. Microneedles 100 are disposed in wells 105 and are advanced into the tissue by microneedle advancers 125. Microneedles 100 are positioned on a periphery of the stapling head assembly 600, outside of the staple lines (or staple arrays).

In operation of the stapling head 600 shown in FIGS. 3, 4, 5 microneedles 100 are inserted into the tissue simultaneously with the staples, by the action of the same staple firing mechanism which advances simultaneously staple advancers 120 and microneedle advancers 125. Microneedles 100 are in alignment with staples 110 and substantially perpendicular to tissue facing surface 160.

Figure 6:
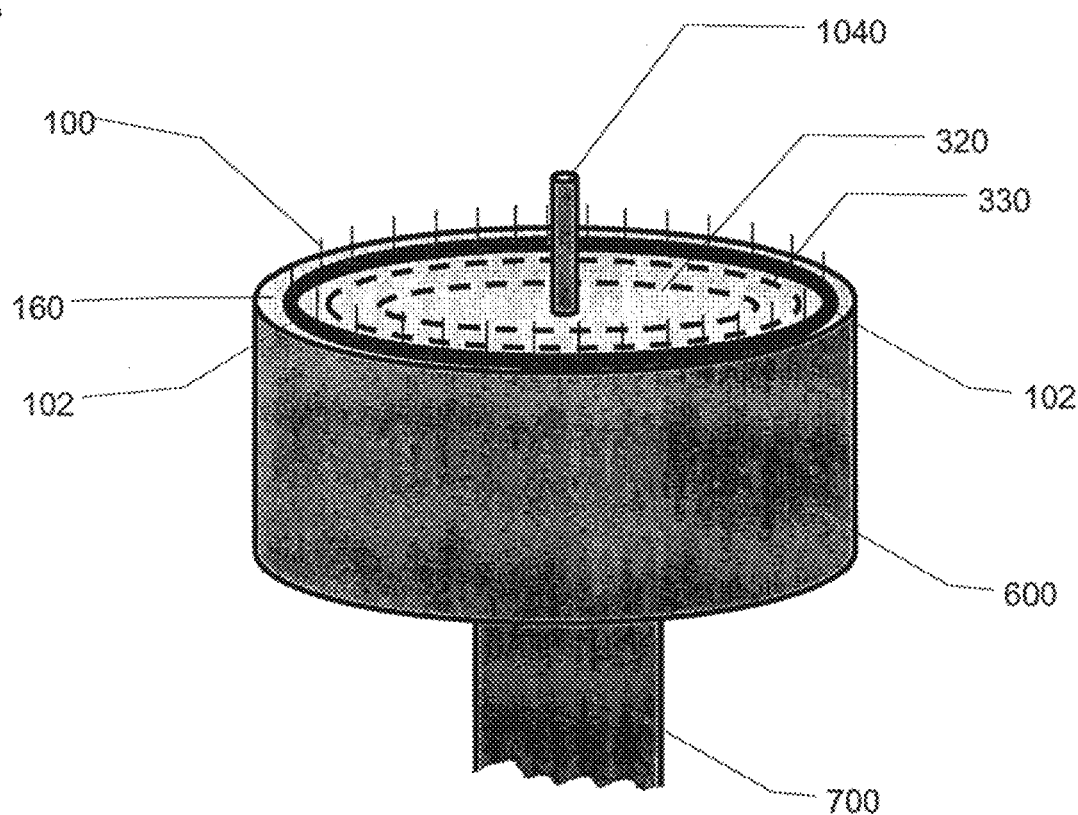
FIG. 6 shows schematic prospective view of one aspect of the circular stapler of the present invention.

Referring now to FIG. 6, another aspect of stapling head assembly 600 is shown in a schematic prospective view, with concentric stapling lines 320 and 330 surrounding moveable shaft 1040 and a concentric array of microneedles 100 positioned on, and perpendicular to, tissue facing surface 160, with microneedles 100 concentric array situated around the larger stapling line 330 on the periphery of stapling head assembly 600, and distally from moveable shaft 1040. Microneedles 100 are disposed on ring-shaped attachment strip 102 positioned concentrically around the larger stapling line 330 on the periphery of stapling head assembly 600.

Figure 7:
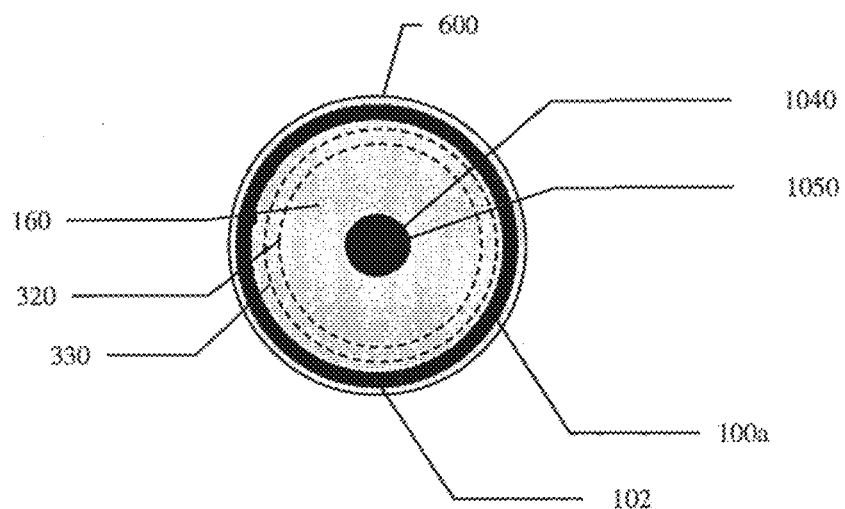
FIG. 7 shows schematic top view of one aspect of the circular stapler of the present invention.
Figure 8:
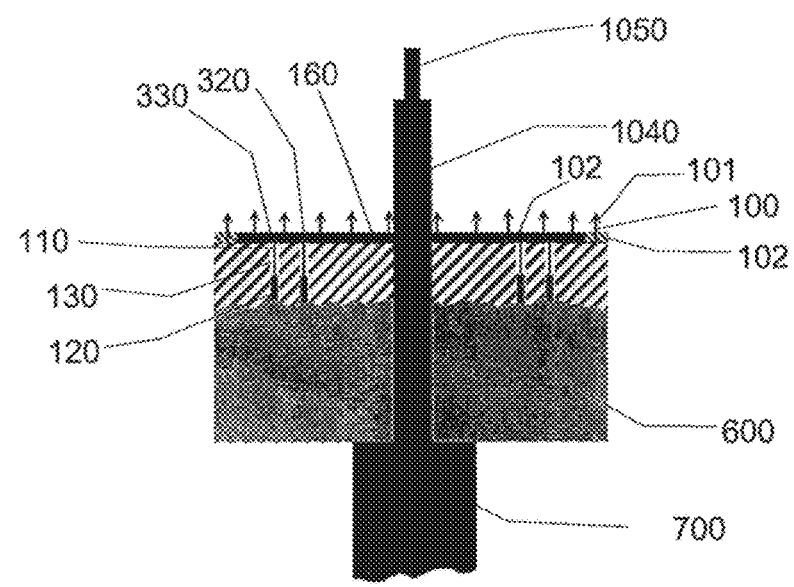
FIG. 8 shows schematic side cross-sectional view of one aspect of the circular stapler of the present invention.

FIG. 7 is showing a schematic top view of stapling head assembly 600 as illustrated in FIG. 6. FIG. 8 is showing a schematic cross-sectional side view of stapling head assembly 600, with staples 110 deployed in channels 130, and microneedles 100 with optional barbed tips 101 positioned on tissue facing surface 160. As shown in FIGS. 6-8, plurality of microneedles 100 are arranged on the periphery of stapling head assembly 600 as a concentric array of microneedles 100, positioned around the larger stapling line 330 and distally from moveable shaft 1040. In one aspect, microneedles 100 are releasably attached to tissue facing surface 160 by ring-shaped attachment strip 102. Staples deployment mechanism is not shown in FIG. 8 for simplification. Microneedles 100 are in alignment with staples 110 and substantially perpendicular to tissue facing surface 160.

Microneedles 100 are detachably supported on ring-shaped attachment strip 102, so that upon insertion into tissue, microneedles 100 break off or detach from attachment strip 102 and stay in the tissue. Microneedles can have a sharpened tip facing the tissue.

Figure 9:
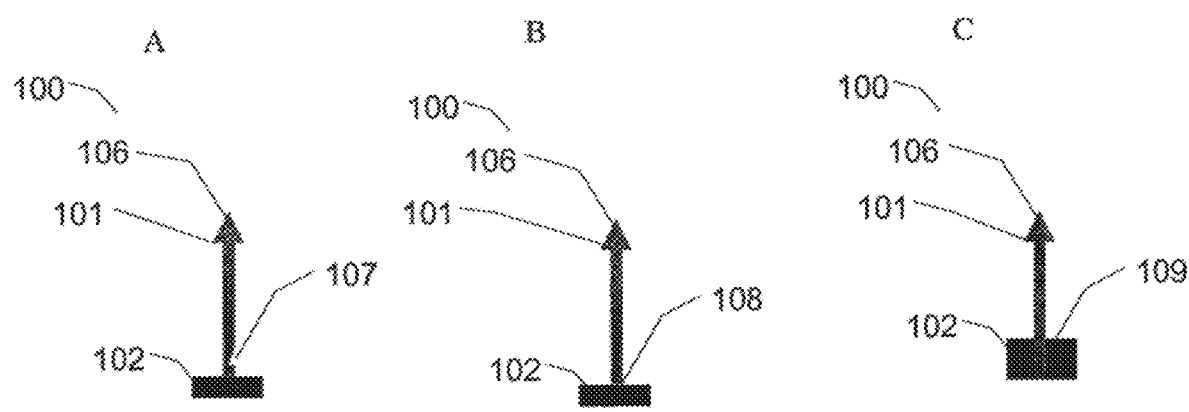
FIG. 9 shows schematic side cross-sectional view of certain aspects of microneedles of the present invention.

Attachment strip 102 is a flat ring-shaped supporting structure disposed on tissue facing surface 160. Preferably it is made of a polymeric material and releasably engages with microneedles 100. Referring now to FIG. 9, several different aspects of microneedles 100 supported on attachment strip 102 are shown. FIG. 9A shows microneedle 100 with sharp tip 106 and optional barb 101 strongly attached to attachment strip 102 at the end opposite the barb 101, with a nick or detent 107 weakening microneedle 100 in the vicinity of microneedle attachment to attachment strip 102. Advantageously, after insertion of microneedle 100 into the tissue and engagement of the barb 101 with the tissue upon closing of the circular stapler, microneedle 100 breaks off at the nick or detent 107 as circular stapler is opened, with microneedle 100 staying in the tissue. Strong attachment of microneedle 100 having detent 107 is performed by adhesives, co-molding, welding, and other methods known to these skilled in the art.

FIG. 9B shows microneedle 100 with sharp tip 106 with optional barb 101 detachably attached to attachment strip 102 at the end opposite the barb 101. The detachability of microneedle 100 from strip 102 is achieved by weak joining of microneedle 100 to strip 102 by adhesives, welding, and other methods known to these skilled in the art in the area 108 between the end of the microneedle 100 opposite the barb 101 and the attachment strip 102. Advantageously, after insertion of microneedle 100 into the tissue and engagement of the barb 101 with the tissue, microneedle 100 separates from attachment strip 102 in the area 108 as circular stapler is opened, with microneedle 100 staying in the tissue.

FIG. 9C shows microneedle 100 with sharp tip 106 and with optional barb 101, detachably attached to attachment strip 102 at the end opposite the barb 101, with detachability achieved by a weak joint formed by a snug insertion of microneedle 100 into a cavity or aperture 109 in attachment strip 102, or direct insertion of microneedle 100 into the attachment strip 102 which can be made of a pierceable material, such as a foam or a gel. Advantageously, after insertion of microneedle 100 into the tissue and engagement of the barb 101 with the tissue, microneedle 100 separates from attachment strip 102 as circular stapler is opened, with microneedle 100 staying in the tissue.

Figure 10:
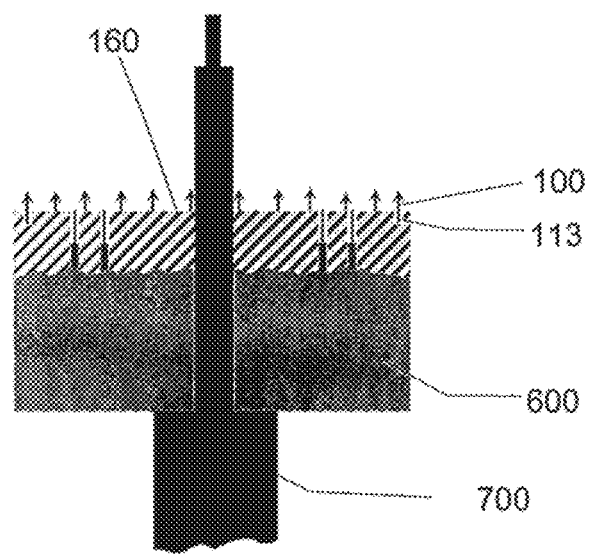
FIG. 10 shows schematic side cross-sectional view of one aspect of the circular stapler of the present invention.

In the embodiment shown in FIG. 10, microneedles 100 are detachably attached directly to stapling head assembly 600 without any attachment strip 102, with detachability achieved by a joint formed by a snug insertion of microneedle 100 into a cavity 113 in tissue facing surface 160. Advantageously, after insertion of microneedle 100 into the tissue and engagement of the barb 101 with the tissue, microneedle 100 separates from stapling head assembly 600 as circular anastomotic stapler is opened and removed, with microneedles 100 staying in the tissue.

In one aspect, a collapsible protector is at least partially surrounding microneedles 100 to prevent microneedle 100 damage prior to closing of the circular stapler and insertion of microneedles 100 into the tissue. Collapsible protector can be made of easily compressible foam. In the embodiment shown in FIG. 11, the attachment strip 102 is made of thick collapsible material, such as a foam, and is sized to completely encapsulate and envelop microneedles 100, thus acting as collapsible protector, to prevent microneedle 100 damage prior to closing of the circular anastomotic stapler and insertion of microneedles 100 into the tissue. Microneedles 100 are releasably supported within the foam of the attachment strip 102, and are released upon compression of attachment strip 102 and insertion of microneedles into the tissue with engagement of microneedle barbs 101 with the tissue, while attachment strip 102 is removed as circular anastomotic stapler is removed upon completion of the stapling.

Figure 12:
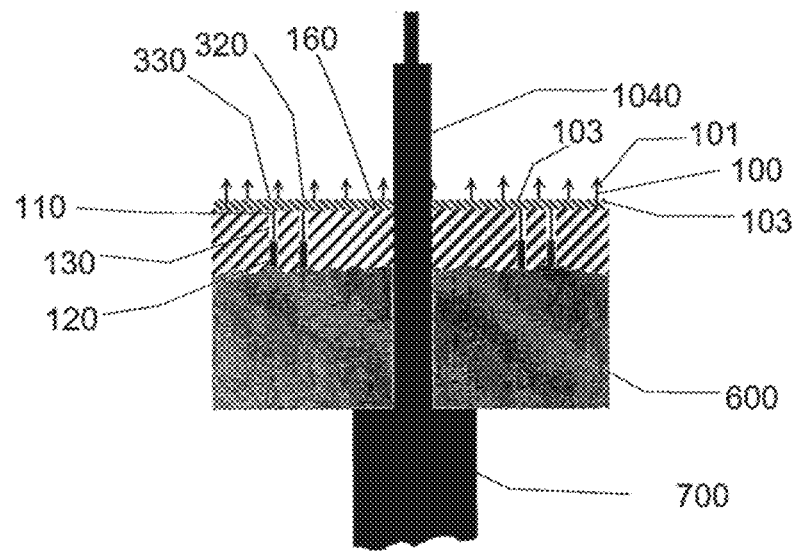
FIG. 12 shows schematic side cross-sectional view of one aspect of the circular stapler of the present invention.

In one aspect, as shown in FIG. 12, a buttress 103 is disposed on the tissue facing surface 160, said buttress 103 supporting microneedles 100. In this aspect, microneedles 100 are configured not to separate from buttress 103 upon deployment of microneedles 100 in the tissue, but are staying attached to buttress 103 as buttress 103 is stapled to tissue. Buttress 103 is a flat, disk-shaped supporting structure made of non-absorbable or preferably absorbable material, such as a synthetic or natural polymer, in a form of woven, non-woven, foam, or molded structure. In one aspect, buttress 103 is covering all tissue facing surface 160 or at least the area including the periphery of stapling head assembly 600 and the staples 110, in other words covering stapling lines 320 and 330 and supporting microneedles 100 concentrically surrounding stapling lines 320 and 330. Upon deployment of staples 110, buttress 103 is attached to tissue layers being joined by the deployed staples 110 which penetrate buttress 103. Upon removal of circular anastomotic stapler, buttress 103 stays attached to joined layers of tissue by staples 110 and continuing supporting microneedles 100 inserted into the tissue. In one aspect, microneedles 100 have optional barbs 101 at the ends distal to tissue facing surface 160, as shown in FIG. 12. In alternative aspects, microneedles 100 have no barbs 101 as microneedles 100 are supported in the tissue by buttress 103.

Use of buttresses and various materials useful for making a buttress are known to these skilled in the arts of surgical stapling. U.S. Pat. No. 6,273,897 "Surgical buttress and surgical stapling apparatus" and U.S. Pat. No. 6,325,810 "Foam buttress for stapling apparatus", both assigned to Ethicon, Inc., describing surgical staplers and buttresses are incorporated by reference herein in their entirety for all purposes.

Figure 13:
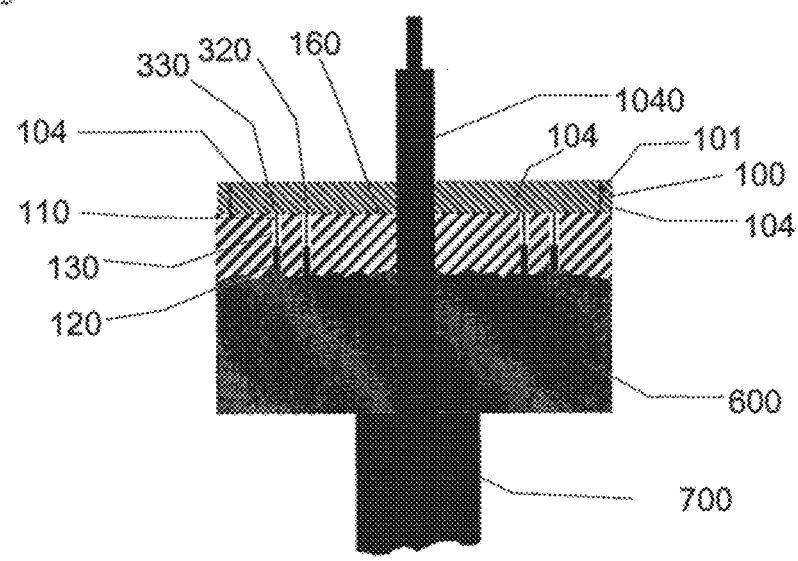
FIG. 13 shows schematic side cross-sectional view of one aspect of the circular stapler of the present invention.

In one aspect, as shown in FIG. 13, a compressible tissue thickness compensator 104 is disposed on the tissue facing surface 160, with tissue thickness compensator 104 supporting microneedles 100. Microneedles 100 are disposed within and are enveloped by compressible tissue thickness compensator 104.

In this aspect, microneedles 100 are configured not to separate from tissue thickness compensator 104 upon deployment of microneedles 100 in the tissue, but are staying attached to tissue thickness compensator 104 as tissue thickness compensator 104 is stapled to tissue. Tissue thickness compensator 104 is a disk-shaped supporting structure made of non-absorbable or preferably absorbable material, such as a synthetic or natural polymer, in a form of woven, non-woven, foam, or molded structure. In one aspect, tissue thickness compensator 104 is covering all tissue facing surface 160 or at least the area including the periphery of stapling head assembly 600 and the staples 110, in other words covering stapling lines 320 and 330 and supporting microneedles 100 concentrically surrounding stapling lines 320 and 330. Upon deployment of staples 110, tissue thickness compensator 104 is attached to tissue layers being joined by the deployed staples 110 which penetrate tissue thickness compensator 104. Upon removal of circular anastomotic stapler, tissue thickness compensator 104 stays attached to joined layers of tissue by staples 110 and continuing supporting microneedles 100 inserted into the tissue. In this In one aspect, microneedles 100 have optional barbs 101 at the ends distal to tissue facing surface 160, as shown in FIG. 13. In alternative aspects, microneedles 100 have no barbs 101 as microneedles 100 are supported in the tissue by compressible tissue thickness compensator 104.

Use of compressible tissue thickness compensators and various materials useful for making compressible tissue thickness compensators, such as foams and fabrics are known to these skilled in the arts of surgical stapling. U.S. Pat. No. 8,657,176 "Tissue thickness compensator for a surgical stapler", published US Patent Application No. 2012/0241505 "Tissue thickness compensators for circular surgical staplers", and US Patent Application NO. 2012/0241503 "Tissue thickness compensators", describing surgical staplers and compressible tissue thickness compensators, all of which are incorporated by reference herein in their entirety for all purposes.

In the aspects of the present invention illustrated in FIGS. 3-5, i.e. wherein microneedles 100 are deployed in wells 105 similar to the staples wells and pushed into the tissue by the same mechanism as the staples, microneedles 100 are deployed simultaneously and synchronously with the deployment of staples and stapling of the tissue layers together.

As will be illustrated below, in the aspects of the present invention shown in FIGS. 6-17, microneedles 100 are deployed as the circular stapler is closed, i.e. as anvil 1000 and stapling head 600 are brought together compressing tissue between them, i.e. prior to the deployment of staples and stapling of the tissue layers together.

Referring now to FIG. 14, a schematic cross-sectional partial view of a portion of circular stapler performing anastomotic joining of tubular tissues T1 and T2 is presented, with the circular stapler corresponding to one shown in FIG. 8, whereby microneedles 100 are supported on attachment strip 102. Anvil 1000 is shown disposed within tubular tissue T1 and connected to stapling head 600 which is disposed within tubular tissue T2. For simplification, the mechanism of staple deployment not shown in FIG. 14.

Figure 14A:
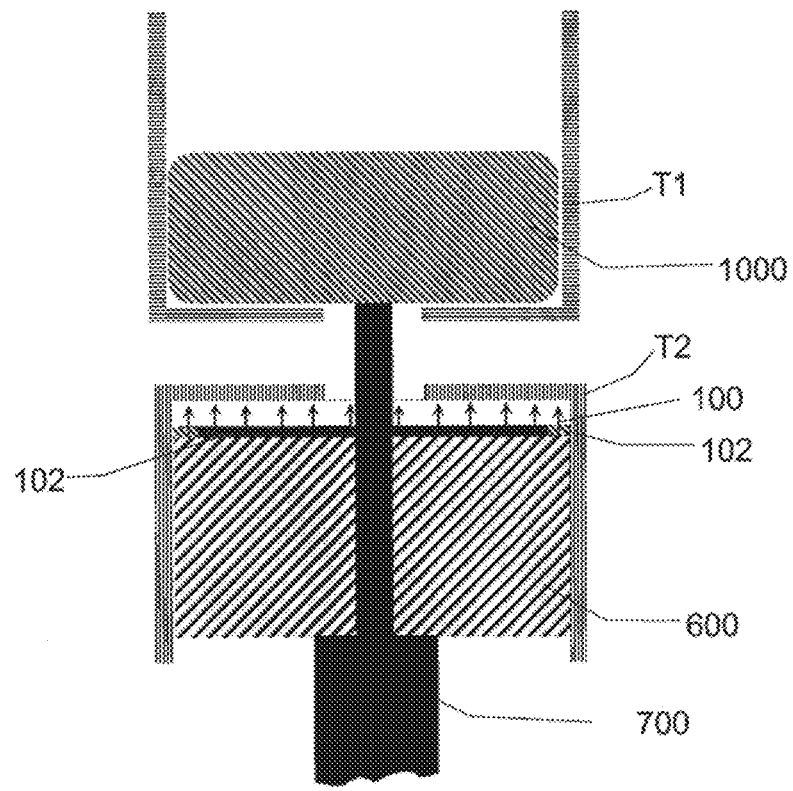
FIGS. 14A-14D show schematic cross-sectional side views of a portion of the circular stapler of the present invention in operation.
Figure 14B:
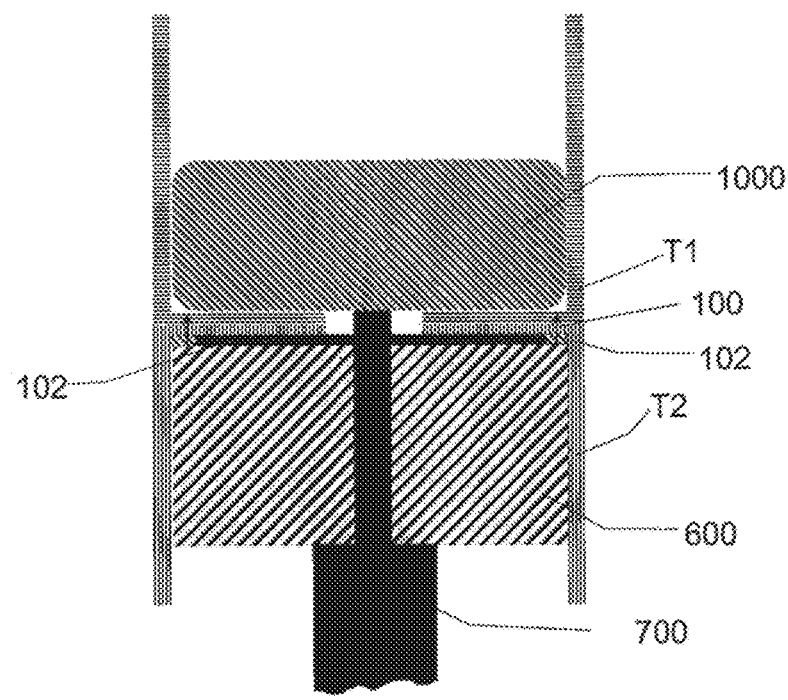
Figure 14C:
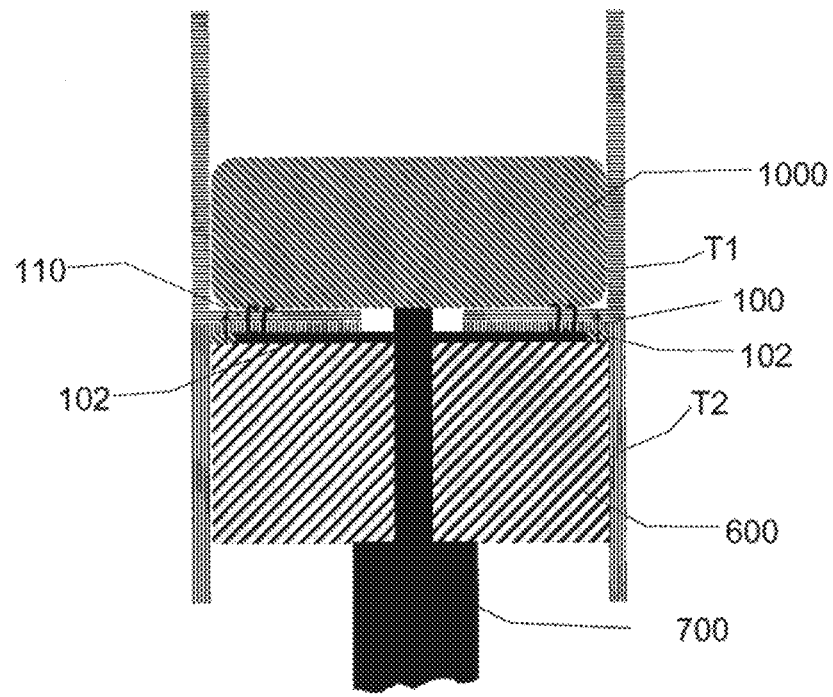
Figure 14D:
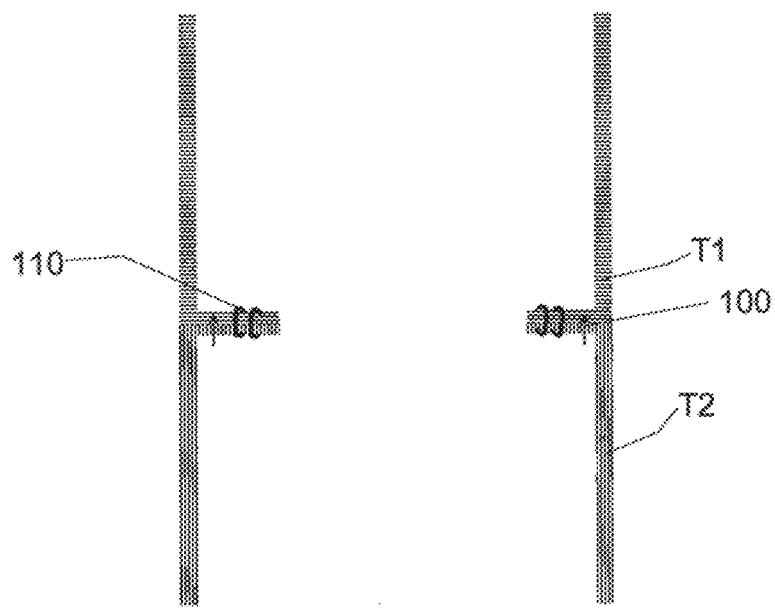

FIGS. 14A-14D illustrate the sequence of performing anastomotic joining of tissues T1 and T2. FIG. 14A shows the position in preparation to performing anastomotic joining of tissues T1 and T2, prior to approximation of anvil 1000 and stapling head 600 to each other. FIG. 14B shows anvil 1000 and stapling head 600 approximated, compressing tissue T1 and T2 between them, with barbed microneedles 100 supported on attachment strip 102 piercing and entering both tissues T1 and T2. Microneedles 100 are inserted into tissue by the force of the approximation of anvil 1000 and stapling head 600 which is compressing tissue T1 and T2. FIG. 14C shows staples 110 fired thus establishing stapled joint between tissues T1 and T2. FIG. 14D shows stapling head 600 and anvil 1000 removed, with established anastomotic joint of tissues T1 and T2 established by staples 110, with barbed microneedles 100 separated from attachment strip 102 (not shown in FIG. 14D) and remaining in both tissues T1 and T2 outside of the stapling area. Sharp tips of microneedles 100 facilitate piercing of tissue layers T1 and T2 by microneedles 100. Optional barbs prevent microneedles 100 from exiting stapled tissue T1 and T2.

Figure 11:
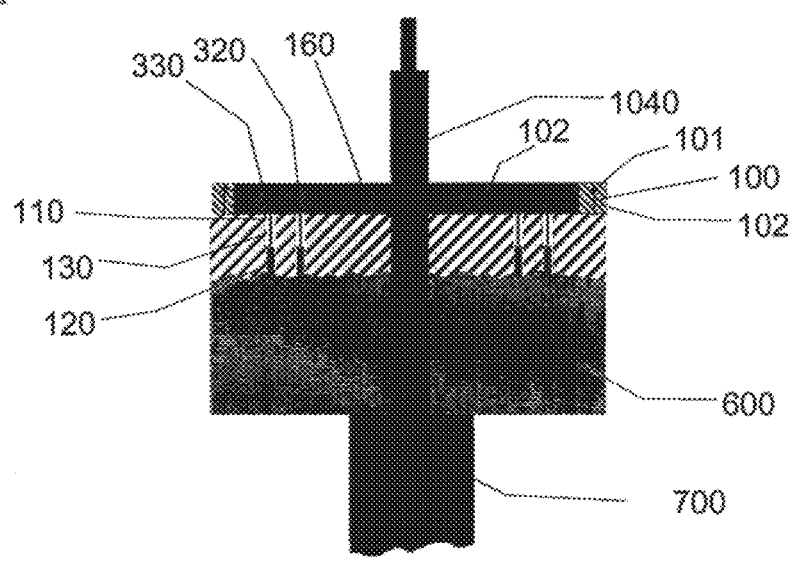
FIG. 11 shows schematic side cross-sectional view of one aspect of the circular stapler of the present invention.

Referring now to FIG. 15, a schematic cross-sectional partial view of a portion of circular stapler performing anastomotic joining of tubular tissues T1 and T2 is presented, with the circular stapler corresponding to one shown in FIG. 11, whereby microneedles 100 are supported on attachment strip 102 which is made of thick collapsible material, such as a foam, and is sized to completely encapsulate and envelop microneedles 100, thus acting as collapsible protector, to prevent microneedle 100 damage prior to closing of the circular anastomotic stapler and insertion of microneedles 100 into the tissue. Anvil 1000 is shown disposed within tubular tissue T1 and connected to stapling head 600 which is disposed within tubular tissue T2. For simplification, the mechanism of staple deployment not shown in FIG. 15.

Figure 15A:
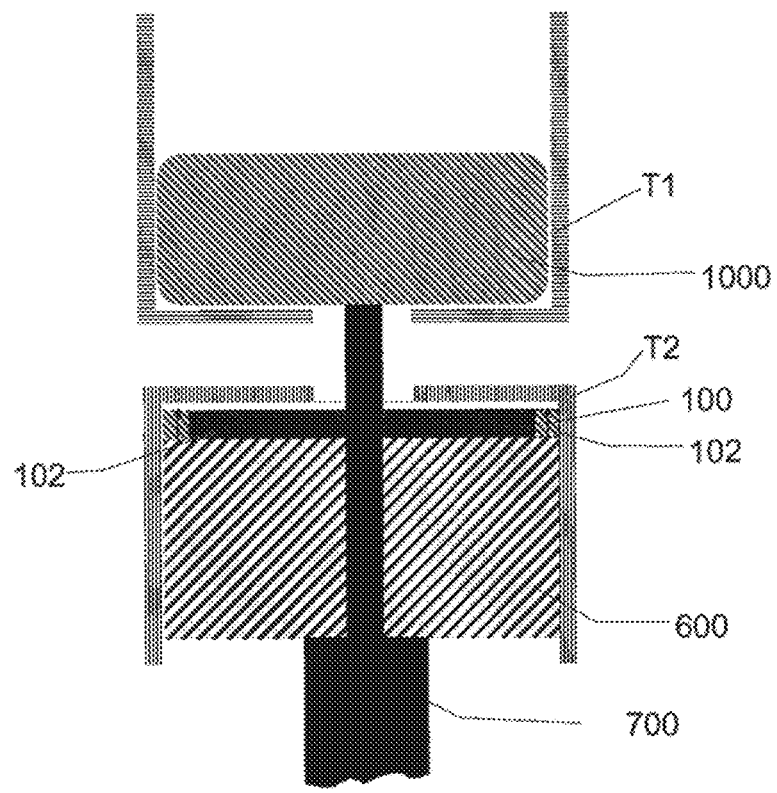
FIGS. 15A-15D show schematic cross-sectional side views of a portion of the circular stapler of the present invention in operation.
Figure 15B:
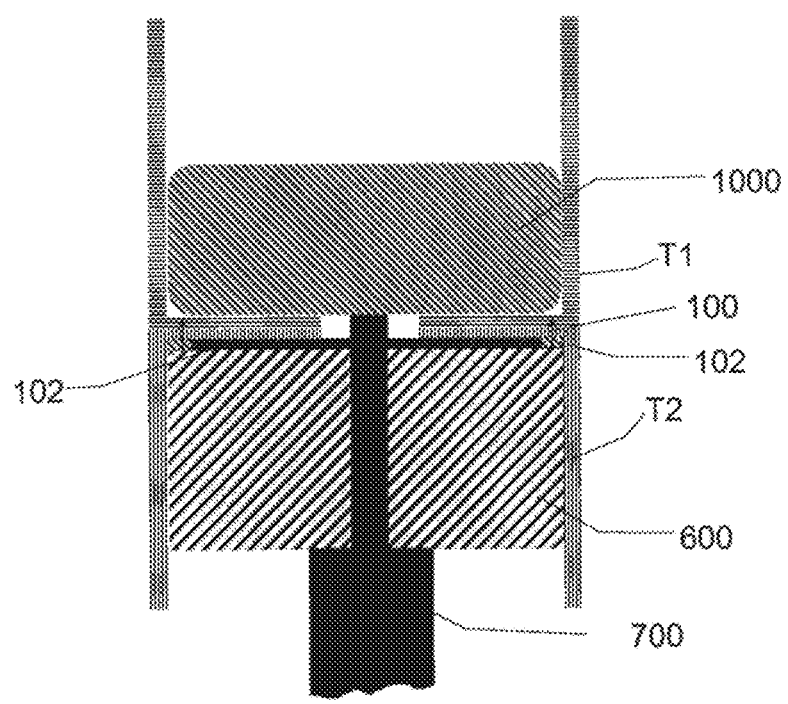
Figure 15C:
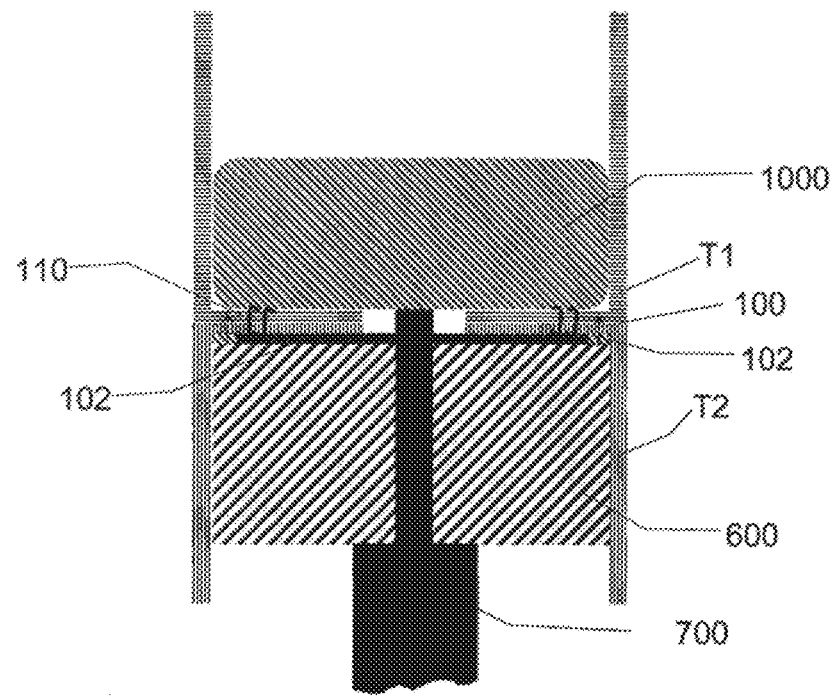
Figure 15D:
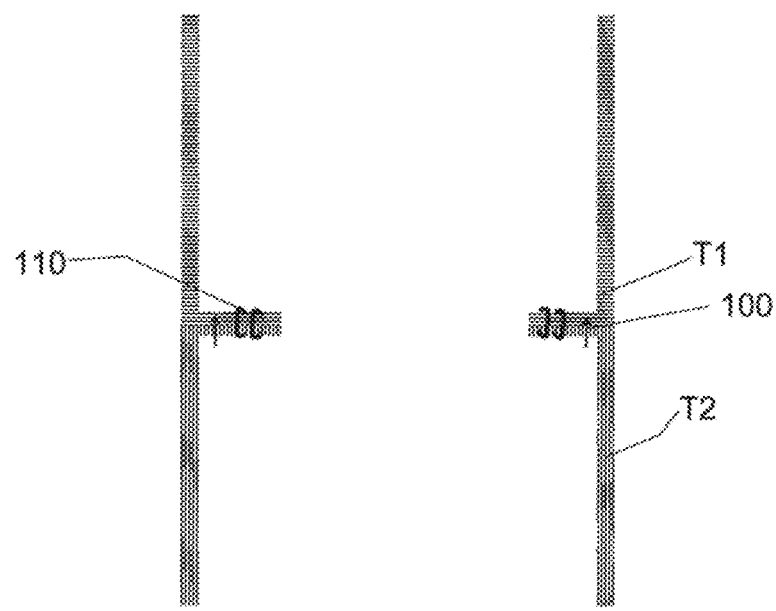

FIGS. 15A-15D illustrate the sequence of performing anastomotic joining of tissues T1 and T2. FIG. 15A shows the position in preparation to performing anastomotic joining of tissues T1 and T2, prior to approximation of anvil 1000 and stapling head 600 to each other. FIG. 15B shows anvil 1000 and stapling head 600 approximated, compressing tissue T1 and T2 between them, and also compressing attachment strip 102, with barbed microneedles 100 supported on attachment strip 102 piercing and entering both tissues T1 and T2. Microneedles 100 are inserted into tissue by the force of the approximation of anvil 1000 and stapling head 600 which is compressing tissue T1 and T2. FIG. 15C shows staples 110 fired thus establishing stapled joint between tissues T1 and T2. FIG. 15D shows stapling head 600 and anvil 1000 removed, with established anastomotic joint of tissues T1 and T2 established by staples 110, with barbed microneedles 100 remaining in both tissues T1 and T2 outside of the stapling area. Sharp tips of microneedles 100 facilitate piercing of tissue layers T1 and T2 by microneedles 100. Optional barbs prevent microneedles 100 from exiting stapled tissue T1 and T2.

Referring now to FIG. 16, a schematic cross-sectional partial view of a portion of circular stapler performing anastomotic joining of tubular tissues T1 and T2 is presented, with the circular stapler corresponding to one shown in FIG. 12, whereby microneedles 100 are supported on a buttress 103. In this aspect, microneedles 100 are configured not to separate from buttress 103 upon deployment of microneedles 100 in the tissue, but are staying attached to buttress 103 as buttress 103 is stapled to tissue. Anvil 1000 is shown disposed within tubular tissue T1 and connected to stapling head 600 which is disposed within tubular tissue T2. For simplification, the mechanism of staple deployment not shown in FIG. 16.

Figure 16A:
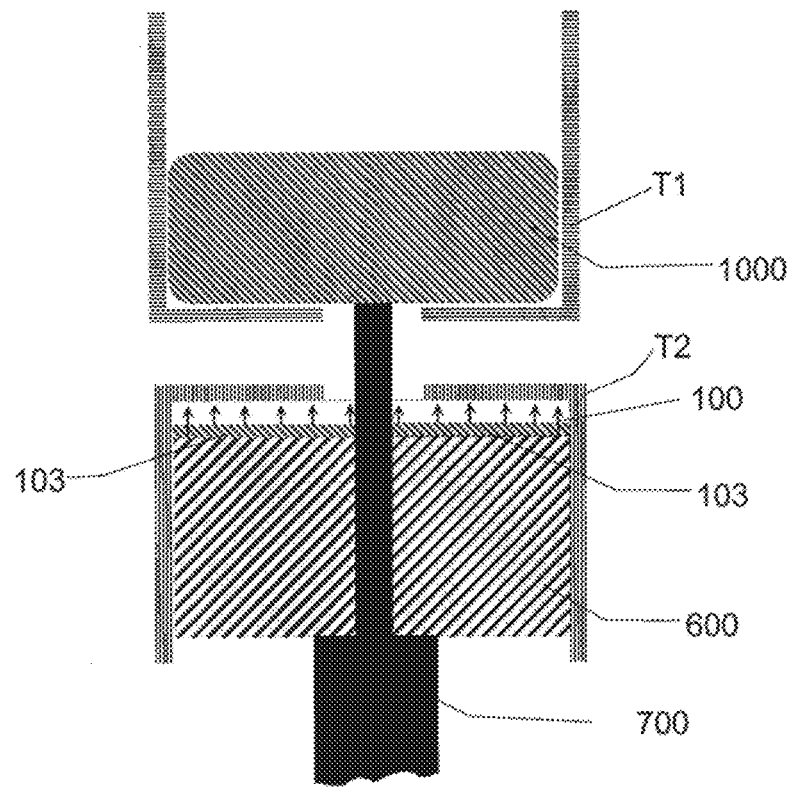
FIGS. 16A-16D show schematic cross-sectional side views of a portion of the circular stapler of the present invention in operation.
Figure 16B:
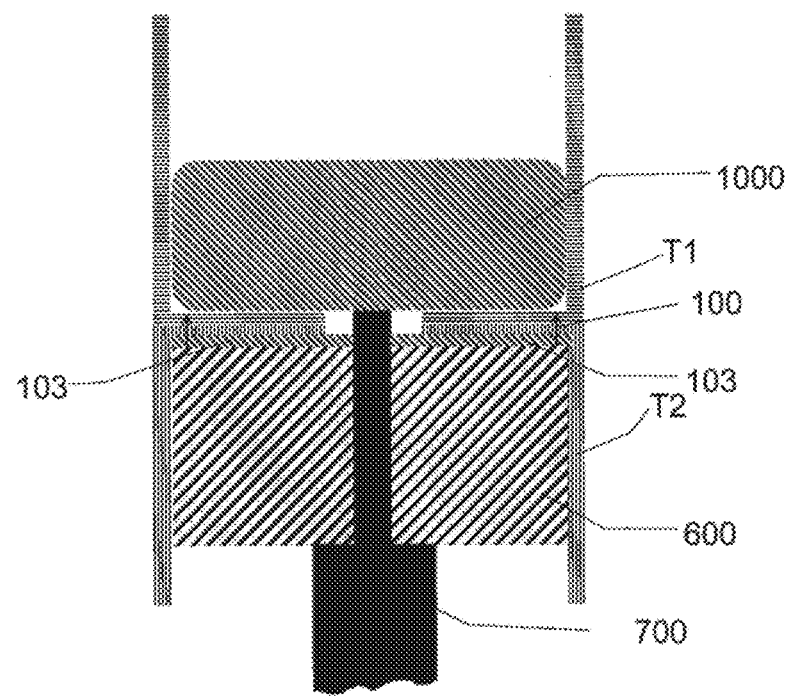
Figure 16C:
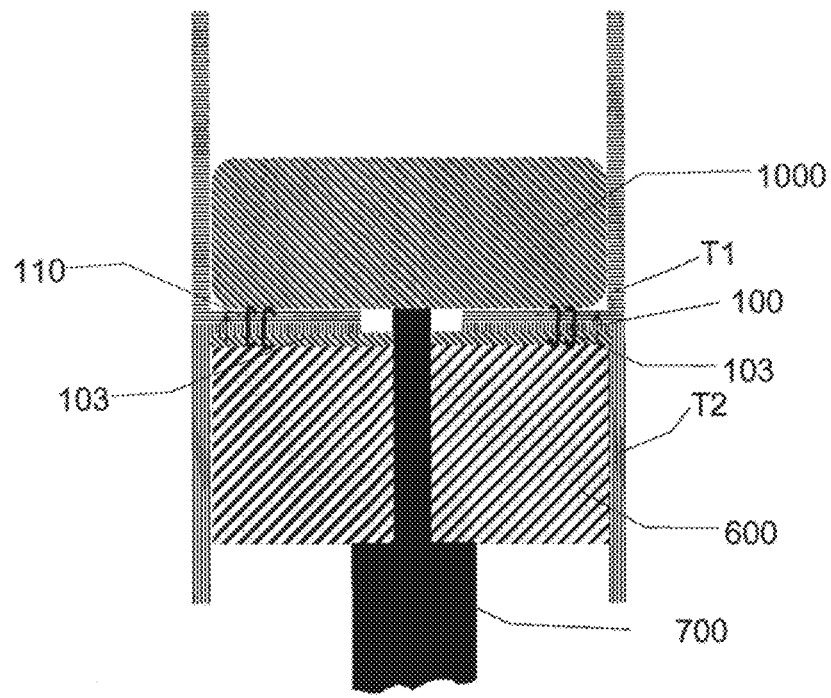
Figure 16D:
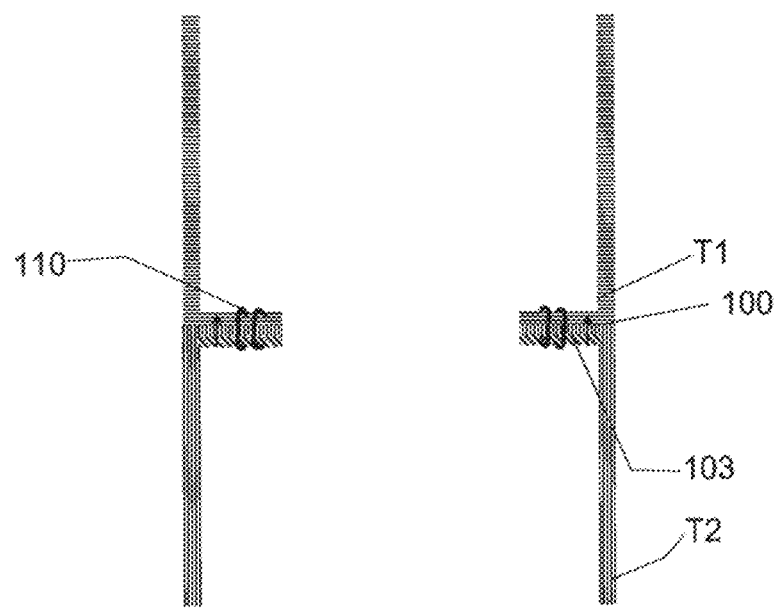

FIGS. 16A-16D illustrate the sequence of performing anastomotic joining of tissues T1 and T2. FIG. 16A shows the position in preparation to performing anastomotic joining of tissues T1 and T2, prior to approximation of anvil 1000 and stapling head 600 to each other. FIG. 16B shows anvil 1000 and stapling head 600 approximated, compressing tissue T1 and T2 between them, with barbed microneedles 100 supported on buttress 103 piercing and entering both tissues T1 and T2. Microneedles 100 are inserted into tissue by the force of the approximation of anvil 1000 and stapling head 600 which is compressing tissue T1 and T2. FIG. 16C shows staples 110 fired thus establishing stapled joint between tissues T1 and T2, with buttress 103 attached to tissue T2 by staples 110. FIG. 16D shows stapling head 600 and anvil 1000 removed, with established anastomotic joint of tissues T1 and T2 established by staples 110, with barbed microneedles 100 remaining in both tissues T1 and T2 outside of the stapling area. Buttress 103 is shown attached to tissue T2 by staples 110 and is supporting microneedles 110. Sharp tips of microneedles 100 facilitate piercing of tissue layers T1 and T2 by microneedles 100. Optional barbs prevent microneedles 100 from exiting stapled tissue T1 and T2. Advantageously, because microneedles 100 are supported on the tissue by buttress 103, barbs are optional in these embodiments. Accordingly, in some aspects of the present invention, there are no barbs on microneedles 100.

Referring now to FIG. 17, a schematic cross-sectional partial view of a portion of circular stapler performing anastomotic joining of tubular tissues T1 and T2 is presented, with the circular stapler corresponding to one shown in FIG. 13, whereby microneedles 100 are supported on compressible tissue thickness compensator 104. In this aspect, microneedles 100 are configured not to separate from tissue thickness compensator 104 upon deployment of microneedles 100 in the tissue, but are staying attached to tissue thickness compensator 104 as tissue thickness compensator 104 is stapled to tissue. Anvil 1000 is shown disposed within tubular tissue T1 and connected to stapling head 600 which is disposed within tubular tissue T2. For simplification, the mechanism of staple deployment not shown in FIG. 17.

Figure 17A:
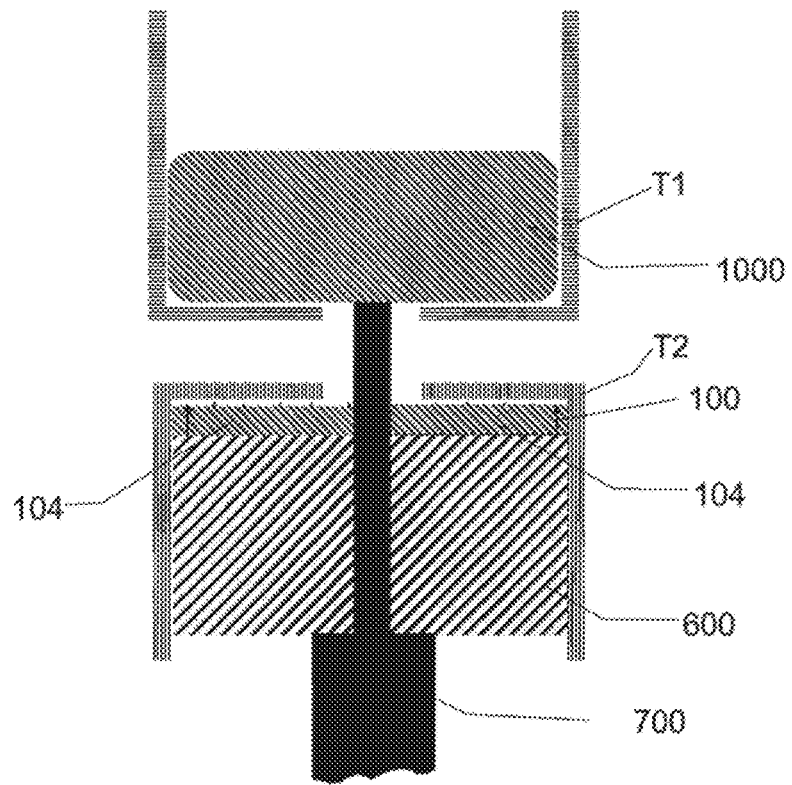
FIGS. 17A-17D show schematic cross-sectional side views of a portion of the circular stapler of the present invention in operation.
Figure 17B:
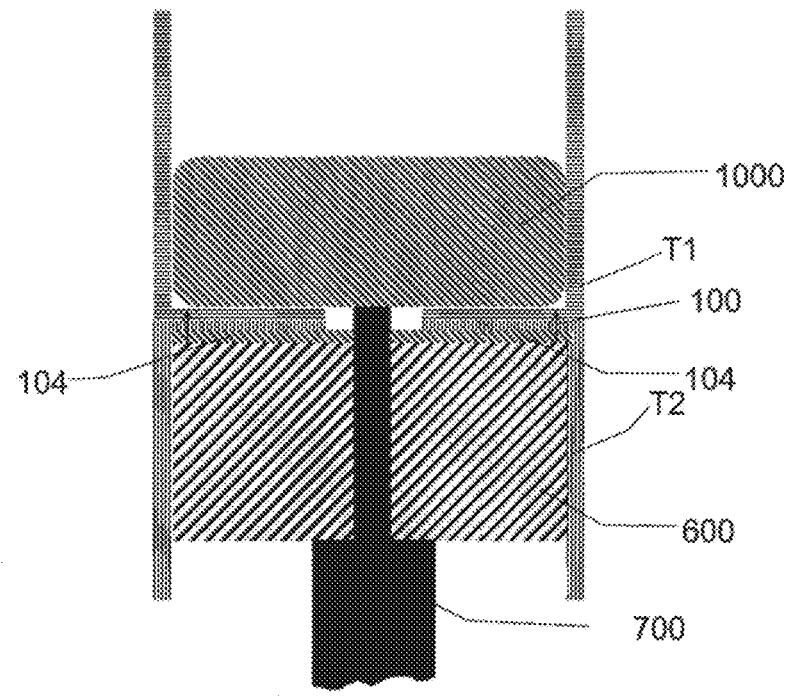
Figure 17C:
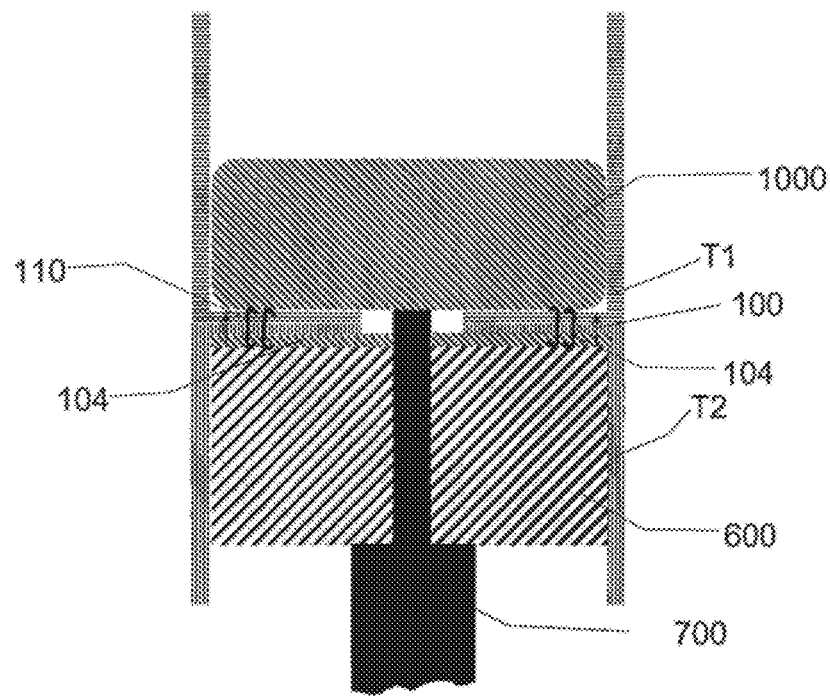
Figure 17D:
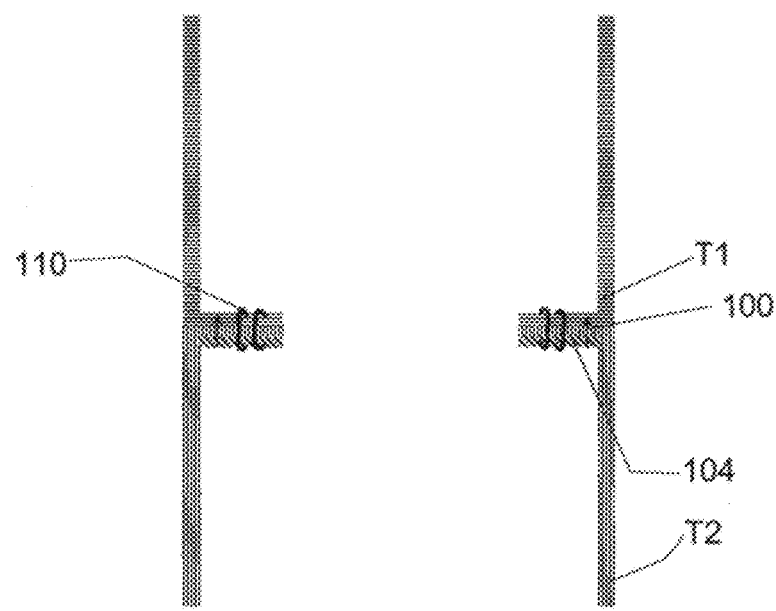

FIGS. 17A-17D illustrate the sequence of performing anastomotic joining of tissues T1 and T2. FIG. 17A shows the position in preparation to performing anastomotic joining of tissues T1 and T2, prior to approximation of anvil 1000 and stapling head 600 to each other. FIG. 17B shows anvil 1000 and stapling head 600 approximated, compressing tissue T1 and T2 between them, with barbed microneedles 100 supported on tissue thickness compensator 104 piercing and entering both tissues T1 and T2. Microneedles 100 are inserted into tissue by the force of the approximation of anvil 1000 and stapling head 600 which is compressing tissue T1 and T2. FIG. 17C shows staples 110 fired thus establishing stapled joint between tissues T1 and T2, with tissue thickness compensator 104 attached to tissue T2 by staples 110. FIG. 17D shows stapling head 600 and anvil 1000 removed, with established anastomotic joint of tissues T1 and T2 established by staples 110, with barbed microneedles 100 remaining in both tissues T1 and T2 outside of the stapling area. tissue thickness compensator 104 is shown attached to tissue T2 by staples 110 and is supporting microneedles 110. Sharp tips of microneedles 100 facilitate piercing of tissue layers T1 and T2 by microneedles 100. Optional barbs prevent microneedles 100 from exiting stapled tissue T1 and T2. Advantageously, because microneedles 100 are supported on the tissue by tissue thickness compensator 104, barbs are optional in these embodiments. Accordingly, in some aspects of the present invention, there are no barbs on microneedles 100.

In all aspects of the present invention, microneedles 100 are disposed in the tissue outside of the staple line and distal to the tissue resection, i.e. with staples 110 positioned between tissue resection areas and microneedles 100.

According to alternative aspects of the present invention, microneedles 100 are disposed on anvil 1000 and not on stapling head 600, using the same mechanisms as described above. In all aspects of the present invention, microneedles 100 are disposed on the periphery of stapling head 600 or anvil 1000.

Barbed and non-barbed microneedles can be manufactured by a variety of techniques known to a skilled artisan, including injection molding, laser cutting, casting, 3D printing, micromachining, embossing, and other known techniques. Microneedles can also be made of a rigid extruded monofilament, cut under angle for sharpness, and optionally barbed by partial surface cutting. In one aspect, semi-rigid extruded monofilament has barbs typical of a barbed suture, with a plurality of barbs present on the microneedle made of extruded monofilament. The strength and dimensional stability of the microneedles are sufficient to penetrate into the tissue without breakage.

Material of construction of the microneedles is any soluble and/or absorbable polymer, synthetic, or natural, and combinations thereof, including, but not limited to, polyesters and/or co-polyesters based on monomers such as lactide, glycolide, p-dioxanone, and combinations thereof; polyvinyl alcohol; gelatin; collagen; fibrin; and combinations thereof; or any other biocompatible, bioabsorbable polymers known to a skilled artisan. In all embodiments, the microneedles are intended to fully absorb into the surrounding tissue within the time period relevant to the wound healing or somewhat longer than the wound healing, i.e. within periods of from about a 1 day to 2-3 days to 1-3 weeks to about 8-10 weeks.

According to embodiments of the present invention, microneedles 100 are from about 50 microns to about 1500 microns in diameter, more preferably from 100 to 1000 microns, such as 200 or 500 microns. According to embodiments of the present invention, microneedles 100 or 100 are from about 100 microns to about 3000 microns long, such as 500 microns or 1000 microns or 2000 microns long. In certain embodiments, there are from about 10 to about 500 or 1000 microneedles, more preferably at least 10 microneedles, most preferably at least 25 or 50 or 100 microneedles arranged in one or several microneedle arrays or groups.

Figure 18:
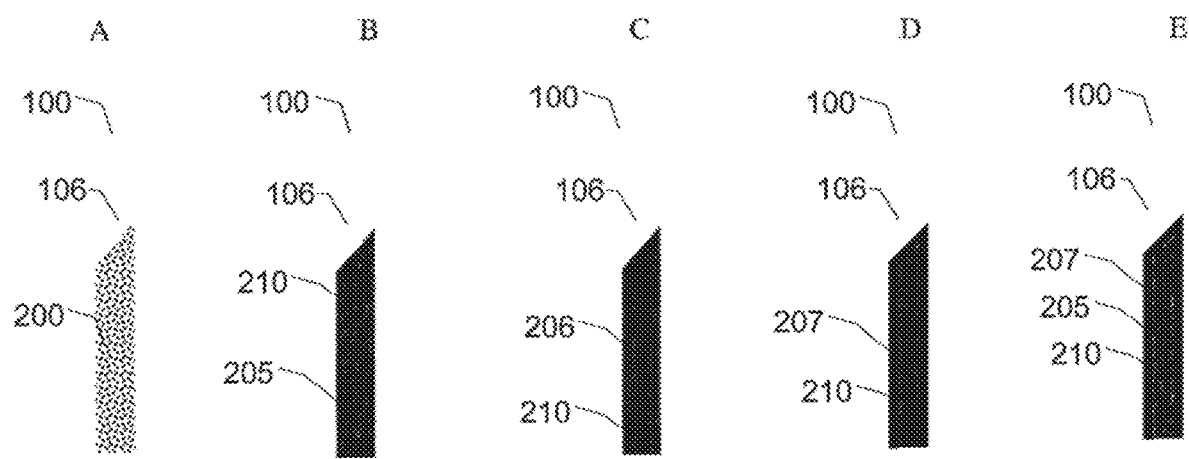
FIG. 18 shows schematic cross-sectional side views of microneedles of the present invention.

Referring now to FIG. 18, microneedles 100 without barbs are shown, having sharpened tips 106. The microneedles 100 can be barb-less as shown, or have barbs which are not shown for simplicity. FIG. 18A shows absorbable microneedle 100 with medicant 200 distributed throughout the microneedle body. The microneedle of FIG. 18A is made of absorbable polymeric material impregnated with the medicant 200. The medicant can be compounded into the polymer, or the microneedle can be exposed to the medicant or the medicant in a carrier solution resulting in penetration and diffusion of the medicant into the microneedle.

FIG. 18B shows absorbable microneedle 100 with medicant in the form of discrete particles or micro-beads or microspheres 205 distributed within polymer 210 comprising microneedle 100 body.

FIG. 18C shows absorbable microneedle 100 with medicant in the form of discrete elongated insert 206 within polymer 210 comprising microneedle 100 body.

FIG. 18D shows absorbable microneedle 100 with medicant in the form of coating 207 coated on the outside of microneedle 100.

FIG. 18E shows absorbable microneedle 100 with medicant in the form of coating 207 coated on the outside of microneedle 100, with the same or different medicant in the form of discrete particles or micro-beads or microspheres 205 distributed within polymer 210 comprising microneedle 100 body. In this embodiment, the medicant in the coating 207 is released first, in the time frame immediately following the insertion of microneedles 100, i.e. over time of a few hours, such as 1 hour, 5 hours, 12 hours, 24 hours, or similar, and whereby the medicant in the form of discrete particles 205 is released over time, i.e. within one or several days or weeks, such as 3 days, 1 week, 2 weeks, 3 weeks, or similar.

In microneedles of the present invention, medicant 200 is released from the microneedles 100 by a variety of mechanisms, i.e. by diffusing out of the microneedle, by release due to the dissolution and/or absorption of the microneedle into the body, or by both mechanisms.

In some embodiments, the medicant is released faster than the full resorption of the microneedle. In one aspect, the medicant is released over 1, 2, or 3 days, while full resorption/dissolution of the microneedle is occurring over 1, 2, or 3 weeks. In another aspect, the medicant is released over 1, 2, or 3 weeks, while full resorption/dissolution of the microneedle is occurring over 3, 5, or 8 weeks. In alternative embodiments, the medicant is released substantially synchronously with the resorption of the microneedle, i.e. the medicant is released over about the same time as the resorption of the microneedle is progressing.

In further alternative embodiments, the medicant is released slower than the dissolution of the microneedle. In one aspect, the microneedle dissolves within 1, 2, or 7 days, while micro particles of the medicant continue releasing the medicant over 1, 2, or 3 weeks.

Figure 19:
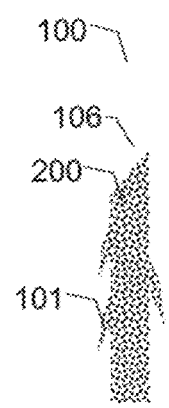
FIG. 19 shows schematic cross-sectional side view of microneedle of the present invention.

Referring now to FIG. 19, microneedle 100 with multiple barbs 101 is shown, with barbs 101 positioned along the microneedle 100 length. Absorbable microneedle 100 is shown having sharpened tip 106 with medicant 200 distributed throughout the microneedle body. The microneedle 100 of FIG. 19 is a short section of a barbed monofilament, essentially a short section of a barbed suture, and is made of absorbable polymeric material impregnated with the medicant 200. In an alternative embodiment (not shown), microneedle 100 of FIG. 19 is further coated with medicant 200.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A circular surgical stapler for anastomotic joining of tissue comprising:
   a) a stapling head connected to an opposing anvil, said stapling head containing a plurality of deployable staples in concentric arrays;
   b) a plurality of solid, barbed, resorbable medicant-releasing microneedles, said microneedles comprising elongated rods having a sharp tissue-penetrating distal end and a proximal end; said microneedles releasably and detachably disposed on or within the stapling head or the anvil;
   wherein said microneedles are configured to break off and detach and to be left in the tissue layers after joining of the tissue layers;
   and
   wherein said medicant is impregnated into or distributed within a polymeric material comprising said microneedle, is coated onto said microneedle, or is a discrete elongated insert within said microneedle.

2. The stapler of claim 1, wherein the microneedles are disposed on a tissue-facing surface of the stapling head on a periphery of the stapling head and outside of the concentric arrays of the deployable staples.

3. The stapler of claim 2, wherein said microneedles further comprise a barb at the distal end thereof and wherein said microneedles are substantially perpendicular to the tissue-facing surface.

4. The stapler of claim 2, wherein said microneedles are releasably supported by an attachment strip disposed on the tissue-facing surface.

5. The stapler of claim 2, wherein the stapling head comprises at least 10 microneedles and wherein said microneedles are from 50 microns to about 1000 microns in diameter and from about 100 microns to about 2500 microns long.

6. The stapler of claim 1, wherein said medicant comprises a drug, an enzyme, a growth factor, an anti-inflammatory agent, a vasodilating agent, a peptide, a protein, a nutrient, an excipient, a cell, or combinations thereof.

7. The stapler of claim 1, wherein the medicant is released over a period of from about 2 hours to about 4 weeks.

* * * * *